US006057361A

United States Patent [19]
Hausheer et al.

[11] Patent Number: 6,057,361
[45] Date of Patent: May 2, 2000

[54] FORMULATIONS AND METHODS OF REDUCING TOXICITY OF ANTINEOPLASTIC AGENTS

[75] Inventors: Frederick H. Hausheer; Thomas J. Dodd, both of Boerne, Tex.

[73] Assignee: BioNumerik Pharmaceuticals, Inc., San Antonio, Tex.

[21] Appl. No.: 09/225,702

[22] Filed: Jan. 6, 1999

Related U.S. Application Data

[60] Division of application No. 08/954,678, Oct. 17, 1997, Pat. No. 5,919,816, which is a continuation-in-part of application No. 08/553,005, Nov. 3, 1995, Pat. No. 5,902,610, which is a continuation-in-part of application No. 08/338,379, Nov. 14, 1994, Pat. No. 5,789,000.

[51] Int. Cl.$^7$ .......................... A61K 31/135; A61K 31/35
[52] U.S. Cl. .......................... 514/460; 514/649; 514/772; 514/946; 514/947
[58] Field of Search ................................... 514/460, 649, 514/772, 946, 947

[56] References Cited

U.S. PATENT DOCUMENTS

| | | |
|---|---|---|
| 4,310,515 | 1/1982 | Granatek et al. . |
| 5,789,000 | 8/1998 | Hausheer et al. . |

OTHER PUBLICATIONS

Leeuwenkamp et al., European Journal of Cancer, vol. 27, No. 10, pp. 1243–1247, Oct. 1991.

Shaw, I.C. and Weeks, M.S., Excretion of Disodium Bis–2–Mercaptoethanesulphonate (Dimesna) in the Urine of Volunteers after Oral Dosing; Eur J Cancer Clin Oncology 23:933–935; 1987.

Levine, Barry S., Henry, Mary C., Port, Curtis D., Richter, Ward R., and Urbanek, Mary A.; Nephrotoxic Potential of cis–Diamminedichloroplatinum and Four Analogs in Male Fischer 344 Rats; JNCI, 67(1):210–206 Jul. 1981.

Arrick, Bradley A., et al. Glutathione Metabolism as a Determinant of Therapeutic Efficacy: A Review. Cancer Research, 44: 4224–4232, Oct. 1984.

Andrews, Paul A., et al. Metallothionein–mediated cisplatin resistance in human ovarian carcinoma cells. Cancer Chemother Pharmacol, 19: 149–154, 1987.

Bajorin, Dean F., et al. Pharmacokinetics of cis–Diamminedichloroplatinum(II) after Administration in Hypertonic Saline. Cancer Research, 46: 5969–5972, Nov. 1986.

Borch, Richard F., et al. Effect of diethyldithiocarbamate rescue on tumor response to cisplatinum in a rat model. Proc. Natl. Acad. Sci. USA, 77:5441–5444, Sep. 1980.

Brock, N., The Development of Mesna for the Inhibition of Urotoxic Side Effects of Cyclophosphamide, Ifosfamide, and Other Oxazaphosphorine Cytostatics. Rec. Res. Cancer Res., 74:20–278, 1980.

Brock, Norbert, et al., Studies on the Urotoxicity of Oxazaphosphorine Cytostatics and its Prevention. Eur. J. Cancer clin. Oncol., 17: 1155–1163, 1981.

Brock, Norbert, et al., Studies on the Urotoxicity of Oxazaphosphorine Cytostatics and its Prevention—III. Profile of Action of Sodium 2–mercaptoethane Sulfonate (Mesna). Eur. J. Cancer Clin. Oncol., 18(12): 1377–1387, 1982.

Brock, Von N., et al., Arzneim Forsch 32: 486–487 (1982).

Brock, N., et al., Pharmacokinetcis and Mechanism of Action of Detoxifying Low–Molecular–Weight Thiols. J. Cancer Res. Clin. Oncol., 108: 87–97, 1984.

Brock, Norbert, et al., The development of mesna for regional detoxification. Cancer Treatment Reviews, 10(Suppl. A): 33–43, 1983.

Burkert, Hans, et al., Clinical overview of mesna. Cancer Treatment Reviews, 10(Suppl. A): 175–181, 1983.

Burkert, H., et al., Bioavailability of Orally Administered Mesna. Arzneim.–Forsch./Drug Res., 34:(II), 1597–1600, 1984.

Campbell, A. Bruce, et al., Plasma Platinum Levels: Relationship to Cisplatin Dose and Nephrotoxicity. Cancer Treatment Reports, 67(2): 169–172, Feb. 1983.

Choie, D. David, et al., Acute and Chronic Cisplatin Nephropathy in Rats. Laboratory Investigation, 44(5):397–402, 1981.

Daugarrd, Gedske, et al., Cisplatin nephrotoxicity a review. Cancer Chemother. Pharmacol., 25: 1–9, 1989.

DeConti, Ronald C., et al., Clinical and Pharmacological Studies with cis–Diamminedichloroplatinum(II). Cancer Research, 33: 1310–1315, Jun. 1973.

Dentino, Mariellen, et al., Long Term Effect of Cis–Diamminedichloride Platinum (CDDP) on Renal Function and Structure in Man. Cancer, 41(4): 1274–1281, Apr. 1978.

Earhart, Robert H., Instability of cis–Dichlorodiammineplatinum in Dextrose Solution. Cancer Treatment Reports, 62(7): 1105–1106, Jul. 1978.

Eastman, Alan, Gluthathione–mediated activation of anticancer platinum (IV) complexes. Biochemical Pharamcology, 36(23): 4177–4178, 1987.

Eastman, Alan, Reevaluation of Interaction of cis–Dichloro(ethylenediamine)platinum(II) with DNA. Biochemistry, 25: 3912–3915, 1986.

Glover, Donna, et al., WR–2721 and High–Dose Cisplatin: An Active Combination in the Treatment of Metastatic Melanoma. Journal of Clinical Oncology, 5(4): 574–578, Apr., 1987.

Goldstein, Robin S., et al., The Nephrotoxicity of Cisplatin. Life Sciences, 32: 685–690, 1983.

(List continued on next page.)

*Primary Examiner*—Richard L. Raymond
*Attorney, Agent, or Firm*—Thomas J. Dodd

[57] ABSTRACT

This invention provides for pharmaceutical formulations of compounds which are useful as protective agents when administered to patients also receiving antineoplastic drugs. The invention also includes methods of reducing the toxicity of various antineoplastic agents by administering an effective amount of the protective agent to a patient receiving one or more antineoplastic agents. The compounds useful as protective agents have either a sulfhydryl moiety or are reducible disulfides.

20 Claims, No Drawings

OTHER PUBLICATIONS

Gonzalez–Vitale, Juan C., et al., The Renal Pathology in Clinical Trials of Cis–Platinum (II)Diamminedichloride. Cancer, 39: 1362–1371, 1977.

Hayes, Daniel M., et al., High Dose Cis–Platinum Diammine Dichloride, Amelioration of Renal Toxicity by Mannitol Diuresis. Cancer, 39: 1372–1381, 1977.

Howell, Stephen B., et al., Intraperitoneal Cisplatin with Systemic Thiosulfate Protection. Annals of Internal Medicine, 97: 845–851, 1982.

Hegedus, L., et al., Chemical reacitivity of cisplatin bound to human plasma proteins. Cancer Chemother. Pharmacol., 20: 211–212, 1987.

Jacobs, Charlotte, et al., Renal Handling of cis–Diamminedichloroplatinum(II). Cancer Treatment Reports, 64(12): 1223–1226, Dec. 1980.

James, C.A., et al., Estimation of mesna and dimesna in plasma and urine by high–performance liquid chromatography with electrochemical detection. Journal of Chromatography, 382: 394–398, 1986.

Jocelyn, Biochemistry of the SH Group. Academic Press, London, New York, 1972.

Kelley, Susan L., et al., Overexpression of Metallothionein Confers Resistance to Anticancer Drugs. Science, 241: 1813–1815, Sep. 1988.

Kempf, S.R., et al., Effective prevention of the nephrotoxicity of cis–platin (CDDP) by administration of sodium 2–mercaptoethane–sulfonate (MESNA) in rats. Br. J. Cancer, 52: 937–939, 1985.

Kociba, Richard J., et al., Acute Toxicologic and Pathologic Effects of Cis–Daimminedichloroplatinum (NSC–119875) in the Male Rat. Cancer Chemotherapy Reports, 55: 1–8, Feb. 1971.

Lemaire, Henry, et al., The Synthesis of 2–Mercaptoethane––sulfonamide. J. Org. Chem., 26: 1330–1331, Apr. 1961.

Markman, Maurie, Intraperitoneal Chemotherapy. Seminars in Oncology, 18(3): 248–254, Jun. 1991.

Leonard, B.J., et al., Antileukaemic and Nephrotoxic Properties of Platinum Compounds. Nature, 234: 43–45, Nov. 1971.

Offerman, Joop J.G., et al., Acute effects of cis–diamminedichloroplatinum (CDDP) on renal function. Cancer Chemother. Pharmacol., 12: 36–38, 1984.

Ormastad, Kari, et al., Pharmacokinetics and Metabolism of Sodium 2–Mercaptoethanesulfonate in the Rat. Cancer Research, 43: 333–338, Jan. 1983.

Ostrow, S., et al., High–Dose Cisplatin Therapy Using Mannitol Versus Furosemide Diuresis: Comparative Pharmacokinetics and Toxicity. Cancer Treatment Reports, 65: 73–78, 1981.

Ozols, Robert F., et al., High–dose Cisplatin in Hypertonic Saline. Annals of Internal Medicine, 100: 19–24, 1984.

Pfeifle, Craig E., et al., High–Dose Cisplatin with Sodium Thiosulfate Protection. Journal of Clinical Oncology, 3(2): 237–244, Feb. 1985.

Pinto, Ann L., et al., Binding of the Antitumor Drug cis––Diamminedichloroplatinum (II) (Cisplatin) to DNA. Biochimica et Biophysica Acta., 780: 167–180, 1985.

Pohl, Von J., et al., Meth. Find. Clin. Pharmacol. 3(Supp. 1): 95–101, 1981.

Perry, M.C., The Chemotherapy Source Book, Williams and Wilkins, 1172 pp., 1992.

Reed, Eddie, et al., Platinum Analogues in Cancer Chemotherapy, Principles and Practice, 465–490, 1990.

Rosenberg, Barnett, et al., Platinum Compounds: A New Class of Potent Antitumor Agents. Nature, 222: 385–386, Apr. 1969.

Rozencweig, Marcel, et al., Cis–diamminedichloroplatinum (II) A New Anticancer Drug. Annals of Internal Medicine, 86: 803–812, 1977.

Safirstein, Robert, et al., Cisplatin Nephrotoxicity. American Journal of Kidney Disease, 8(5): 356–367, Nov. 1986.

Sidau, Beate, et al., Determination of sodium 2–mercaptoethanesulphonate by high–performance liquid chromatography using post–column reaction colorimetry or electrochemical detection. Journal of Chromatography, 311: 234–238, 1984.

Symposium: Cisplatin: Contemporary Treatment Approaches. Seminars in Oncology, 16(Suppl. 6): 1–128, 1989.

Thomson, A.J., The Interactions of Platinum Compounds with Biological Molecules. Rec. Res. Cancer Res., 48: 38–62, 1974.

FORMULATIONS AND METHODS OF REDUCING TOXICITY OF ANTINEOPLASTIC AGENTS

CROSS-REFERENCE TO RELATED APPLICATIONS

This application is a Divisional of application Ser. No. 08/954,678, filed Oct. 17, 1997, now U.S. Pat. No. 5,919, 816, which is a Continuation-In-Part of application Ser. No. 08/553,005, filed Nov. 3, 1995, now U.S. Pat. No. 5,902, 610, which is a Continuation-In-Part of application Ser. No. 08/338,379, filed Nov. 14, 1994, now U.S. Pat. No. 5,789, 000.

FIELD OF THE INVENTION

This invention relates to pharmaceutical formulations of antineoplastic drugs and a detoxifying agent. The detoxifying agent is a compound which has one or more sulfhydryl moieties, or a reducible disulfide, and serves to reduce of eliminate the toxic side effects of the antineoplastic drug with which it is formulated or administered. The invention also relates to methods of reducing the toxicity of various antineoplastic agents by administering to a patient an effective amount of the detoxifying agent before, simultaneously with and/or after administration of the antineoplastic agent.

BACKGROUND OF THE INVENTION

Since the discovery of the antineoplastic properties of the nitrogen mustards more than 50 years ago, cancer chemotherapy has been an ever expanding area of scientific endeavor, and has been a critical component of cancer treatment along with surgery and radiation therapy. Where chemotherapy was once accepted only as a means to extend survival time for those patients diagnosed as incurable by surgery and/or radiation therapy, it is now a recognized modality of treatment in nearly all of the more than two thousand variations of cancer.

Modern cancer chemotherapy typically involves a combination of two or three different drugs, and the advances in technology and medical knowledge have greatly improved a patient's chances of recovery in many forms of cancer. The role of antineoplastic agents in cancer therapy varies widely depending upon the form of cancer. For example, chemotherapy is often the primary course of therapy in cancers of the ovary, testis, breast, bladder, and others, in leukemias and lymphomas, and is generally employed in combination with radiation therapy in the treatment of a large number of sarcomas, melanomas, myelomas, and others. In contrast, chemotherapy is often used only as a last resort or as a palliative treatment for most solid tumors, such as carcinomas of the pancreas and lung. There are exceptions within each class of tumor or other neoplasm.

Chemotherapeutic agents, which are commonly referred to throughout this specification as "antineoplastic agents" are classified into a number of diverse groups. The vast majority of these agents act as cytotoxic drugs, and each member of a specific group is postulated to typically exert its cytotoxic effects through a similar biological mechanism. However, it is important to note that a complete understanding of the biological and biochemical mechanisms of action of antineoplastic drugs are not fully known. The mechanisms of action recited in this specification are based upon the current state of the art, and each of these postulated mechanisms may or may not be important to the mechanism of actual cytotoxicity of the drug, or the manner in which the toxic incidences are allayed by the protective agents recited herein.

Unfortunately, nearly all of the antineoplastic agents in use today have the potential to produce significant toxic effects on normal healthy cells apart from the desired killing effects on cancer cells. Drug toxicity can be severe enough to create life-threatening situations, which requires the coadministration of other drugs, the reduction and/or discontinuation of the antineoplastic drug, or the performance of other prophylactic maneuvers, any of which may impact negatively on the patient's treatment and/or the quality of life. Many times, the failure to achieve control of a patient's disease is due to the measures which must be taken to reduce the unwanted toxicity of the antineoplastic agent on healthy cells.

CLASSIFICATION OF ANTINEOPLASTIC DRUGS

As of January 1997, more than seventy commercial antineoplastic agents have been approved for use in the United States. Even more antineoplastic agents are approved for usage overseas. There are also over two hundred investigational new drugs which are undergoing evaluation as antineoplastic agents in clinical trials in the United States and overseas. In addition, thousands of newly discovered compounds are evaluated every year as potential antineoplastic agents.

Currently, there are approximately twenty recognized classes of approved antineoplastic drugs. The classifications are generalizations based on either a common structure shared by particular drugs, or are based on a common mechanism of action by the drugs. Although some drugs fall into two or more classes, in general, the accepted classifications are as follows (the classifications are listed in no particular order):

Structure-Based Classes

1. Fluoropyrimidines
2. Pyrimidine Nucleosides
3. Purines
4. Platinum Analogues
5. Anthracyclines/Anthracenediones
6. Podophyllotoxins
7. Camptothecins
8. Hormones and Hormonal Analogues
9. Enzymes, Proteins and Antibodies
10. Vinca Alkaloids
11. Taxanes

Mechanism-Based Classes

1. Antihormonals
2. Antifolates
3. Antimicrotubule Agents
4. Alkylating Agents (Classical and Non-Classical)
5. Antimetabolites
6. Antibiotics
7. Topoisomerase Inhibitors
8. Antivirals
9. Miscellaneous Cytotoxic Agents The above classifications of cytotoxic agents will no doubt expand in the years to come as research efforts increase. As described above, many of the approved antineoplastic agents in use today fall into two or more classifications, with many of the structurally similar agents having similar mechanisms of action, and vice versa.

A partial listing of some of the commonly known commercially approved (or in active development) antineoplastic agents by classification is as follows:

1. Fluoropyrimidines—5-FU, Fluorodeoxyuridine, Ftorafur, 5'-deoxyfluorouridine, UFT, S-1 Capecitabine;
2. Pyrimidine Nucleosides—Deoxycytidine, Cytosine Arabinoside, 5-Azacytosine, Gemcitabine, 5-Azacytosine-Arabinoside;
3. Purines—6-Mercaptopurine, Thioguanine, Azathioprine, Allopurinol, Cladribine, Fludarabine, Pentostatin, 2-Chloro Adenosine;
4. Platinum Analogues—Cisplatin, Carboplatin, Oxaliplatin, Tetraplatin, Platinum-DACH, Ormaplatin, CI-973, JM-216;
5. Anthracyclines/Anthracenediones—Doxorubicin, Daunorubicin, Epirubicin, Idarubicin, Mitoxantrone;
6. Epipodophyllotoxins—Etoposide, Teniposide;
7. Camptothecins—Irinotecan, Topotecan, 9-Amino Camptothecin, 10,11-Methylenedioxy Camptothecin, 9-Nitro Camptothecin, TAS 103;
8. Hormones and Hormonal Analogues—Diethylstilbestrol, Tamoxifen, Toremefine, Tolmudex, Thymitaq, Flutamide, Bicalutamide, Finasteride, Estradiol, Trioxifene, Droloxifene, Medroxyprogesterone Acetate, Megesterol Acetate, Aminoglutethimide, Testolactone and others;
9. Enzymes, Proteins and Antibodies—Asparaginase, Interleukins, Interferons, Leuprolide, Pegaspargase, and others;
10. Vinca Alkaloids—Vincristine, Vinblastine, Vinorelbine, Vindesine;
11. Taxanes—Paclitaxel, Docetaxel.

Mechanism-Based Classes

1. Antihormonals—See classification for Hormones and Hormonal Analogues, Anastrozole;
2. Antifolates—Methotrexate, Aminopterin, Trimetrexate, Trimethoprim, Pyritrexim, Pyrimethamine, Edatrexate, MDAM;
3. Antimicrotubule Agents—Taxanes and Vinca Alkaloids;
4. Alkylating Agents (Classical and Non-Classical)-Nitrogen Mustards (Mechlorethamine, Chlorambucil, Melphalan, Uracil Mustard), Oxazaphosphorines (Ifosfamide, Cyclophosphamide, Perfosfamide, Trophosphamide), Alkylsulfonates (Busulfan), Nitrosoureas (Carmustine, Lomustine, Streptozocin), Thiotepa, Dacarbazine and others;
5. Antimetabolites—Purines, pyrimidines and nucleosides, listed above;
6. Antibiotics—Anthracyclines/Anthracenediones, Bleomycin, Dactinomycin, Mitomycin, Plicamycin, Pentostatin, Streptozocin;
7. Topoisomerase Inhibitors—Camptothecins (Topo I), Epipodophyllotoxins, m-AMSA, Ellipticines (Topo II);
8. Antivirals—AZT, Zalcitabine, Gemcitabine, Didanosine, and others;
9. Miscellaneous Cytotoxic Agents—Hydroxyurea, Mitotane, Fusion Toxins, PZA, Bryostatin, Retinoids, Butyric Acid and derivatives, Pentosan, Fumagillin, and others.

The objective of all antineoplastic drugs is to eliminate (cure) or to retard the growth and spread (remission) of the cancer cells. The majority of the above listed antineoplastic agents pursue this objective by possessing primary cytotoxic activity, effecting a direct kill on the cancer cells. Other antineoplastic drugs stimulate the body's natural immunity to effect cancer cell kill. The literature is replete with discussions on the activity and mechanisms of all of the above drugs, and many others.

The primary difficulty and cause for concern with any antineoplastic drug is its toxicity to normal, healthy cells. All of the above listed drugs (and those drugs currently under development) have the potential to mediate serious and often life-threatening toxic side effects even when given in therapeutically effective dosages. Although extensive efforts have been made to develop antineoplastic drugs which are safe to use in effective doses, there are nearly always toxic side effects associated with such drugs.

Manifestation of the toxic side effects of antineoplastic drugs is generally consistent within each class. One notable exception is the platinum analogues, where the toxicities of the two currently approved drugs exhibit different primary toxic manifestations (the primary toxicity of cisplatin is renal, while carboplatin toxicity affects the bone marrow).

With some exceptions, the primary toxicity of many antineoplastic agents affects the rapidly dividing cells, namely those found in bone marrow and the upper gastrointestinal (GI) tract. Other primary and secondary toxicities may also be manifested, some of which are reversible, with others being permanent. The major toxicities of each drug are listed below in Table 1, with abbreviation keys following the table.

TABLE 1

| TX→ Drug ↓ | BM | GI | RT | NT | DT | LT | PT | HYP | MUC | MISC |
|---|---|---|---|---|---|---|---|---|---|---|
| NM | 3 | 3 | — | — | 2,3 | — | — | 1,2 | 2,3 | — |
| OX | 3 | 2 | 1 | — | 3 | — | 2 | 1 | 2 | a |
| BS | 3 | 1 | — | — | 1 | 1 | 2 | 1 | — | — |
| NU | 3 | 1 | DL | 1 | 1 | 2 | 2 | — | — | — |
| TT | 3 | 1 | — | — | 1 | — | — | 1 | — | — |
| TX | 3 | 2 | — | 2 | 3 | 1 | — | 2 | 2 | b,e |
| VCR | — | 1 | 2 | DL | 3 | — | — | — | — | c,d |
| VBL | 2 | 1 | 2 | 2 | 2 | — | — | — | 2 | c,d |
| VOR | 2 | 1 | 2 | 2 | 2 | — | — | — | 2 | d |
| MTX | 3 | 2 | 3 | 2 | 2 | 2 | 2 | 2 | 3 | — |
| CIS | 2 | 3 | DL | 2 | 2 | — | — | 2 | — | c |
| CARB | 3 | 3 | 1 | 1 | 2 | — | — | 2 | — | c |
| PT | 2,3 | 3 | 1 | 1 | 2 | — | — | 2 | — | c |
| CPT | DL | 2,3 | 1 | 1 | 2 | 1 | — | — | 3 | — |
| PUR | 3 | 2 | 1 | — | 1 | 2 | — | — | — | — |
| PYR | 2 | 1 | — | 2 | 1 | 2 | 2 | 1 | 1 | — |
| POD | 3 | 2 | — | — | 1 | — | — | 1 | — | — |
| ANTH | 3 | 3 | — | — | 3 | — | — | 2 | 3 | e,f |
| 5-FU | 3 | 3 | — | — | 2 | — | — | 1 | 3 | f |
| AB | 1–3 | 2–3 | — | — | 2–3 | 1–2 | 1–3 | 2–3 | 2–3 | a,f |

Abbreviations

TX—Toxicity  
GI—Gastrointestinal  
NT—Neurologic  
LT—Liver  
HYP—Sensitivity  
NM—Nitrogen Mustards  
BS—Busulfan  
TT—Thiotepa  
VCR—Vincristine  
VOR—Vinorelbine  
CIS—Cisplatin  
PT—Other Platinum Complexes  
PUR—Purines BM—Bone Marrow  
RT—Renal  
DT—Dermatologic  
PT—Pulmonary  
MUC—Mucositis  
OX—Oxazaphosphorines  
NU—Nitrosoureas  
TX—Taxanes  
VBL—Vinblastine  
MTX—Methotrexate  
CARB—Carboplatin  
CPT—Camptothecins  
PYR—Pyrimidines

TABLE 1-continued

POD—Epipodophyllotoxins     ANTH—Anthracyclines
AB—Other Antibiotics

Levels of Toxicity—1 = mild or rare, 2 = moderate, 3 = severe, DL = dose limiting.
Miscellaneous toxicities—a = hemorrhagic cystitis; b = musculoskeletal pain; c = hypotension; d = hypothyroidism; e = cardiac toxicity (dose limiting in the anthracyclines); f = radiation recall.

Specific manifestations of the above listed toxic side effects are available in any of a number of oncology textbooks, publications, patents, and other printed matter. Detailed mechanisms of action and toxicity, both proven and postulated, are also recited in detail throughout the prior art. An overview of these mechanisms is set forth below to outline the metabolism of the antineoplastic drugs, and their effects on malignant, as well as on healthy, tissue.

Mechanisms of Action (Actual and Theoretical)

1. Antihormonals

As their name suggests, the antihormonal antineoplastic drugs exert cytotoxic activity by blocking hormone action at the end-receptor organ. Several different types of neoplasms require hormonal stimulation to propagate cell reproduction. The antihormonal agents, by blocking hormone action, deprive the neoplastic cells of a necessary stimulus to reproduce. As the cells reach the end of their life cycle, they die normally, without dividing and producing additional malignant cells.

Antihormonal drugs have been used with varying degrees of success as treatments for malignancies of the breast, uterus, prostate, testis, and other gender specific organs. Antihormonal drugs generally target androgen receptors in men, and estrogen or progesterone receptors in women. Recently, much research has been devoted to the development of aromatase inhibitors, which indirectly lower estrogen blood levels by blocking the conversion of androgens to estrogens. Antihormonal antineoplastic agents are essentially classified as steroidal or non-steroidal.

Toxicity of antihormonal antineoplastic agents is generally mild to moderate. Since the agents are usually close analogues of natural physiologic agents, they are relatively specific in their mechanism of action, and do not interfere with DNA synthesis, which minimizes the severe side effects seen in most all antineoplastic agents.

Manifestations of toxicity in antihormonal therapy include those effects normally associated with hormone deficiencies, such as hot flashes, weight gain (and weight loss), skin rashes, acne, and others. Nausea and vomiting may occur occasionally, but GI distress is normally mild to moderate and does not normally require dose reduction. Antihormonal therapy is normally limited to patients who exhibit positive responses to hormones.

2. Antifolates

Antifolates exert cytotoxic activity by inhibiting the action of dihydrofolate reductase (DHFR), a critical enzyme in cell reproduction. It is well known that DHFR reduces dihydrofolates to their active, fully reduced tetrahydro form. The tetrahydrofolates act as coenzymes in the de novo synthesis of purines, which are critical precursors to DNA. Depletion of tetrahydrofolate pools also inhibits thymidylate biosynthesis, which blocks the conversion of deoxyuridine phosphate (dUMP) to deoxythymidine phosphate (dTMP), a DNA nucleotide precursor.

Although a number of antifolate drugs have been approved for use in the United States, only one, Methotrexate, is a commercially approved antineoplastic agent. The other approved antifolates are used primarily as anti-infective drugs, due to their propensity to bind to bacterial DHFR with much greater strength and frequency than human DHFR. Methotrexate itself has also been used in the treatment of rheumatoid arthritis, psoriasis, and related inflammatory type diseases, as well as against cancers of the breast, uterus, testis, ovary, and against various forms of leukemia. Single agent Methotrexate is curative against choriocarcinoma, a rare type of cancer.

Antifolates produce a wide range of assorted toxic and other untoward effects. Hematologic toxicity is a major dose-limiting toxicity associated with methotrexate and other antifolates. Other toxic and untoward effects associated with antifolates include neurotoxicity, which is sometimes severe and irreversible; gastrointestinal toxicities, mainly mucositis, nausea, diarrhea, vomiting, anorexia, and others; hepatic toxicity; dermatologic toxicity, often manifested by rashes, alopecia, and tissue inflammation; pulmonary toxicity; renal toxicity; and other untoward toxic side effects. Antifolates are generally recognized as drugs with low therapeutic indices and high incidences of toxic side effects.

3. Antimicrotubule Agents

Antimicrotubule agents interfere with cell division by disrupting the normal functionality of the cellular microtubules. Microtubules are critical elements of the cell, playing an important role in separation of the duplicate chromosomes during cell division, as well as being responsible for many interphase cellular functions, such as maintenance of cell shape and scaffolding, intracellular transport, secretion, neurotransmission, and others.

The two classes of antineoplastic agents which influence microtubules are the Taxanes (Paclitaxel and Docetaxel are the representative agents of this class) and the Vinca Alkaloids (Vincristine, Vinblastine and Vinorelbine are approved members of this class).

Taxanes and Vinca Alkaloids are naturally or semisynthetically derived analogues of naturally occurring compounds derived from plants. In particular, Taxanes are derived from the needles and twigs of the European yew (*Taxus baccata*), or the bark of the Pacific yew (*Taxus brevifolia*). The most widely known Taxanes at this time are paclitaxel (Taxol®) and docetaxel (Taxotere®), which are widely marketed as antineoplastic agents.

Vinca Alkaloids include Vincristine (Oncovin®), Vinblastine (Velban®) and Vinorelbine (Navelbine®), and are derived generally from the periwinkle plant (*Cantharanthus roseus*). These drugs are also widely marketed as antineoplastic drugs.

Although their mechanisms of action are different, both Taxanes and Vinca Alkaloids exert their biological effects on the cell microtubules. Taxanes act to promote the polymerization of tubulin, a protein subunit of spindle microtubules. The end result is the inhibition of depolymerization of the microtubules, which causes the formation of stable and nonfunctional microtubules. This disrupts the dynamic equilibrium within the microtubule system, and arrests the cell cycle in the late $G_2$ and M phases, which inhibits cell replication.

Like Taxanes, Vinca Alkaloids also act to affect the microtubule system within the cells. In contrast to Taxanes, Vinca Alkaloids bind to tubulin and inhibit or prevent the polymerization of tubulin subunits into microtubules. Vinca Alkaloids also induce the depolymerization of microtubules, which inhibits microtubule assembly and mediates cellular metaphase arrest. Vinca Alkaloids also exert effects on nucleic acid and protein synthesis; amino acid, cyclic AMP, and glutathione synthesis; cellular respiration; and exert immunosuppressive activity at higher concentrations.

Both Taxanes and Vinca Alkaloids are toxic compounds having a low therapeutic index. Neurotoxicity and myelosuppression are among the most commonly reported clinical toxicities of these drugs.

Taxanes have been shown to cause a number of different toxic and untoward side effects in patients. The most well-known and severe adverse effects of Taxanes are neurotoxicity and hematologic toxicity, particularly severe neutropenia and thrombocytopenia. Taxanes also cause hypersensitivity reactions in a large percentage of patients; GI effects (nausea, diarrhea and vomiting are common); alopecia; and other untoward effects at the recommended dosages.

Vinca Alkaloids have been associated primarily with neurotoxic effects (the primary adverse effect in patients receiving Vincristine); hematologic toxicity (leukopenia is often severe and dose-limiting in the case of Vinblastine); gastrointestinal effects (nausea, diarrhea and vomiting); alopecia; tissue irritation and necrosis, particularly at the injection site; and other harmful, untoward effects.

4. Alkylating Agents

As the name implies, alkylating agents generally exert cytotoxic activity by alkylating DNA, directly interfering with the reproductive cycle of the cell. As noted in the general listing above, antineoplastic alkylating agents fall into numerous subclasses based on the general structure and mechanism by which they act to alkylate DNA.

Several subclasses of antineoplastic alkylating agents are marketed as chemotherapeutic agents. The most well-known are the nitrogen mustards, which include Chlorambucil, Mechlorethamine, Melphalan, Uracil Mustard, and others.

Oxazaphosphorines are a subtype of the nitrogen mustards and include Ifosfamide, Cyclophosphamide, Trophosphamide and others. Other types of antineoplastic drugs which act as alkylating agents, and which are commercially available as of the date of this application include alkylsulfonates (Busulfan) and nitrosoureas (Carmustine, Lomustine and, to some extent, Streptozocin). Other antineoplastic drugs also possess the ability to alkylate DNA and/or RNA. Dacarbazine and Procarbazine are currently approved drugs in the United States which act as alkylators of DNA.

Antineoplastic alkylating agents produce a wide range of assorted toxic and other untoward side effects. Hematologic toxicity is a major dose-limiting toxicity associated with all alkylating agents, and is often severe. Other toxic and untoward effects associated with alkylating agents include neurotoxicity; gastrointestinal toxicities, mainly nausea, diarrhea, vomiting, anorexia, and others; hepatic toxicity; dermatologic and local area sensitivity, often manifested by rashes, alopecia, and tissue inflammation and necrosis; pulmonary effects; genitourinary effects (hemorrhagic cystitis is often severe in patients receiving cyclophosphamide therapy); and other untoward toxic side effects. Antineoplastic alkylating agents are universally recognized as drugs with low therapeutic indices and high incidences of toxic side effects.

5. Antimetabolites

Antimetabolites generally exert cytotoxic activity by substituting fraudulent nucleotides into cellular DNA, thereby disrupting cellular division, or by inhibition of critical cellular enzymes, which prevents replication of DNA. Antimetabolites are necessarily comprised of purine (guanine or adenosine) or pyrimidine (cytidine or thymidine) bases, with or without the attached sugar moiety.

Purine antimetabolites are widely used antileukemic drugs, particularly in the treatment of various forms of childhood leukemia. 6-Mercaptopurine (6-MP) has been administered as a treatment for acute lymphoblastic leukemia (ALL) since the mid-1940s. 6-Thioguanine (6-TG) is currently used as a remission inducer in acute myelogenous leukemia (AML). Azathioprine, which is a prodrug of 6-MP, is widely used as an immunosuppressant agent in clinical transplantation. In general, purine antimetabolites are not effective against solid tumors, probably due to the extended lifespan of solid tumor cells compared to leukocytes.

Like other cytotoxic agents, purine antimetabolites also affect the function of normal, healthy cells. The cells most affected by the purine antimetabolites are those rapidly proliferating cells, which have relatively short lifespans, namely the cells found in bone marrow and the upper GI tract.

Purine antimetabolites generally produce a narrow range of toxic and other untoward effects. Hematologic toxicity is a major dose-limiting toxicity associated with 6-mercapto purine, Azathioprine, 6-thioguanine, and other purine antimetabolites. In particular, leukopenia, anemia, and thrombocytopenia have been widely reported effects of these drugs. Other toxic and untoward effects associated with purine antimetabolites include gastrointestinal toxicities, mainly nausea, diarrhea and vomiting; hepatic toxicity; and other untoward toxic side effects. Purine antimetabolites are generally recognized as drugs with low therapeutic indices and high incidences of toxic side effects.

In general, the nucleoside analogues all undergo phosphorylation, in vivo, usually by deoxycytidine kinase to their corresponding nucleotides. In this active form, the drugs are all potent antimetabolites, and are postulated to inhibit one or more enzymes necessary for DNA replication. Many of the antineoplastic nucleosides are cell-cycle specific, acting in the S phase, and perhaps at the $G_1$-S border. Some of the enzymes which the antineoplastic antimetabolites are thought to inhibit include ribonucleotide reductase, DNA polymerase, thymidylate synthetase, uracil riboside phosphorylase, DNA primase, and others. Because of their inhibition of cellular replication enzymes, many of the antineoplastic nucleosides also exhibit antiviral activity.

Nucleoside antimetabolites produce a wide range of assorted toxic and other untoward effects. Hematologic toxicity is a major dose-limiting toxicity associated with all antineoplastic nucleosides, and is often severe. Other toxic and untoward effects associated with nucleosides include neurotoxicity, which is sometimes severe and irreversible; gastrointestinal toxicities, mainly nausea, diarrhea, vomiting, anorexia, and others; hepatic toxicity; dermatologic toxicity, often manifested by rashes, alopecia, and tissue inflammation; pulmonary toxicity; and other untoward toxic side effects. Antineoplastic nucleosides are generally recognized as drugs with low therapeutic indices and high incidences of toxic side effects.

6. Anthracyclines/Anthracenediones

The antineoplastic drugs of this class also possess antibiotic activity, and were originally developed for such purposes. Although the primary mechanism of action of these compounds is uncertain, it has been postulated that they act by inhibiting Topoisomerase II (Topo II) by the formation of cleavable complexes. Other mechanisms are also postulated to account for the wide spectrum of activity of the anthracyclines.

Because of their broad spectrum of activity, anthracyclines and anthracenediondiones have been extensively studied and reported on throughout the last 25 years. There are currently 3 of these agents approved for use in the US (Doxorubicin, Daunorubicin and Mitoxantrone), and two more (Epirubicin and Idarubicin) are approved for use in Europe.

Like other cytotoxic agents, antineoplastic anthracyclines and anthracenediones also affect the function of normal, healthy cells. In particular, the use of these agents has been associated with cardiac toxicity of a type not observed with other antineoplastic agents. Cardiac toxicity is not common (about 20% experience significant problems), but may become chronic and life threatening. Congestive heart failure and other equally severe cardiac diseases occur occasionally in patients receiving anthracycline chemotherapy. In most cases, the adverse cardiac effects are associated with cumulative doses, and in some cases, the effects are irreversible.

Antineoplastic anthracyclines and anthracenediones can generally produce other toxic and untoward effects. Hematologic toxicity is a major dose-limiting toxicity associated with all antineoplastic anthracyclines and anthracenediones. In particular, leukopenia, anemia, and thrombocytopenia have been widely reported effects of these drugs. Other toxic and untoward effects associated with antineoplastic anthracyclines and anthracenediones include gastrointestinal toxicities, mainly mucositis, with nausea, diarrhea and vomiting also frequent; alopecia, which occurs in nearly all patients; severe local tissue damage after extravasation; and other untoward toxic side effects. Antineoplastic anthracyclines and anthracenediones, although having a very broad spectrum of activity, are generally recognized as drugs with low therapeutic indices and high incidences of toxic side effects.

Previous means of combating the toxic effects of the anthracyclines and anthracenediones were nonexistent. Dose reduction or discontinuance of the drug was necessary, adversely affecting the probability of remission or cure. Recently, an experimental drug, ICRF 187, which metabolizes to form a diamide analog of EDTA, has shown some efficacy in ameliorating the cumulative cardiac toxicity of the anthracyclines and anthracenediones.

7. Other Antibiotics

Antineoplastic antibiotics exert their cytotoxic activity through diverse mechanisms. Pentostatin is a purine analogue and acts as an antimetabolite of that class. Bleomycin is a glycopeptide with a molecular weight on nearly 1500 Daltons, and oxidatively cleaves DNA. Actinomycin (also known as Dactinomycin) inhibits RNA and protein synthesis. Plicamycin (Mithramycin) binds to DNA, and Mitomycin and Streptozocin are DNA alkylating agents.

Toxicities associated with antibiotics are similar to other agents with similar mechanisms of action. Hematologic toxicity is quite common with these drugs and is at times severe and dose- limiting. Most of theses drugs are also extremely irritating to tissues, so local extravasation is a concern. In addition, Mithramycin has been associated with a thrombocytopenia induced hemorrhagic syndrome, particularly with prolonged use or high doses of the drug.

Antineoplastic antibiotics are one of the oldest classes of oncology drugs (Actinomycin was introduced into the clinic in 1954), and are still widely used in the treatment of pediatric neoplasms (Actinomycin), testicular neoplasms (Bleomycin), and any of a number of other solid tumors.

8. Topoisomerase Inhibitors

Topoisomerase inhibitors are relatively newly introduced antineoplastic agents, with many more agents currently in various stages of research and development. As more information is developed concerning the Topoisomerases, more agents which inhibit these enzymes will no doubt be studied.

Topoisomerases (hereinafter referred to as Topo I and Topo II) are ubiquitous cellular enzymes which initiate transient DNA strand breaks during replication to allow for free rotation of the strands. The functionality of these enzymes is critical to the replication process of DNA. Without them, the torsional strain in the DNA helix prohibits free rotation, the DNA strands are unable to separate properly, and the cell eventually dies without dividing. Topo I links to the 3'-terminus of a DNA single strand break, while Topo II links to the 5'-terminus of a double strand DNA break.

Epipodopyllotoxins

Epipodophyllotoxins inhibit the action of Topo II. Natural podophyllotoxin is derived from the mayapple and mandrake plants, and extracts of those plants were a source of folk medicine for several centuries. The discovery of antineoplastic properties of both naturally occurring podophyllotoxin and the semi-synthetic epipodophyllotoxins dates back more than 30 years.

Naturally occurring podophyllotoxin has no glucoside ring, and the C4 position on the E-ring is a methoxy moiety. Although the mechanism of action is not fully understood, it has been postulated that the E-ring hydroxy is responsible for inducing double strand DNA breaks by inhibiting the Topo II, while the glucoside moiety is thought to prevent the synthetic drug derivatives from interfering with spindle microtubule assembly.

Etoposide (and Etoposide Phosphate, which is a water soluble prodrug of Etoposide) is currently used in therapy for a variety of cancers, including testicular neoplasms, lung cancers, lymphomas, neuroblastoma, AIDS related Kaposi's Sarcoma, Wilms' Tumor, various types of leukemia, and others. Teniposide is a relatively new drug which was approved by FDA and launched commercially in the United States in 1992 as therapy for refractory childhood leukemia. Teniposide has also exhibited activity against bladder cancer, lymphomas, neuroblastoma, small cell lung cancer, and certain CNS tumors, although it is not approved for such uses.

Both Etoposide and Teniposide are poorly water soluble (less than 10 $\mu$g/mL), and must be formulated with organic solvents for practical IV delivery. Etoposide is also available in an oral dosage form, as a liquid filled capsule.

The primary dose-limiting toxicity of the epipodophyllotoxins is neutropenia, which is often severe, particularly among patients who have been treated with other antineoplastic agents or radiation. Other hematologic toxicities are commonly reported, as are alopecia, GI distress, neurological toxicity, sensitivity reactions, and others. Further, some patients receiving etoposide have suffered congestive heart failure and/or myocardial infarction, which has been attributed many times to the large volume of saline diluent (and in some cases, the speed of the delivery) used to deliver the drug.

Podophyllotoxins exhibit complex pharmacokinetic properties. Etoposide decays into at least 6 identified metabolites, in vivo. It is known that at least two of these metabolites, the glucuronide and the trans-hydroxyacid metabolites possess little cytotoxic activity, and have been postulated to be responsible for the hematologic toxicity of the drug. Since etoposide phosphate is rapidly converted to etoposide, the same metabolites, toxicities, and pharmacokinetic properties are also attributed to the prodrug.

Teniposide has not been studied as extensively as etoposide, but is presumed to have similar properties.

Camptothecins

Although Camptothecins have been known for more than 30 years, their usefulness as antineoplastic agents has only been discovered recently. The gap between discovery and introduction is due mainly to the very poor water solubility exhibited by these compounds. For almost two decades after discovery of the active compound, research was directed towards the discovery of more highly water soluble camptothecins, since administration would be facilitated.

Researchers formulated the lipophilic drugs with sodium hydroxide in an effort to increase the water solubility of the drugs for administration. Unfortunately, these formulations were essentially inactive and also very toxic in vivo. It was discovered in the mid-1980s that in basic pH conditions, camptothecin derivatives hydrolyzed, with the E-ring lactone opening to form a carboxylate anion. This form of the compounds was discovered to have only one-tenth or less the antineoplastic activity of the lactone form, and was also discovered to be highly toxic to healthy cells.

Much research has been devoted since this discovery to developing water soluble camptothecin derivatives which remained in their active lactone form. Along these lines, the recently approved Irinotecan (CPT-11) and Topotecan were developed. Irinotecan is a water soluble prodrug of the highly active, highly lipophilic derivative of CPT known as SN38 (10-hydroxy-7-ethyl CPT). Topotecan incorporates a 9-dimethylaminoethyl moiety of the 10-hydroxy derivative of CPT.

Like many other antineoplastic agents, the primary toxicities of CPT derivatives are hematologic toxicity and GI distress. Irinotecan has been associated with severe diarrhea, which is often dose limiting, as well as neutropenia, mucositis, other GI distress, alopecia and elevated liver function. Toxicities of Topotecan are similar, although the diarrhea is not normally severe.

Camptothecins are generally recognized as drugs with low therapeutic indices and high incidences of toxic side effects. Coadministration of a protective agent which reduces the toxic side effects of camptothecins will provide for a safer and more effective chemotherapeutic regimen. This may even allow higher doses of the antineoplastic drug to be given, thereby increasing the probability of success of treatment.

9. Platinum Complexes

Since the discovery of their antineoplastic properties more than 30 years ago, platinum complexes have been developed as therapeutic agents for many different types of solid tumors. Two such complexes, cisplatin and carboplatin, are in widespread use today, both as single agents and in combination therapy for tumors of the testis, ovary, lung, bladder, and other organs.

The mechanism of action of platinum complexes has been widely studied. Platinum complexes have been discovered to bind covalently to DNA, thereby disrupting DNA function, effecting direct cell kills. Platinum complexes also freely bind to proteins, and it is postulated that protein-bound platinum my also affect DNA.

Toxicity manifestations of cisplatin are entirely different than the toxicity of carboplatin. Cumulative, dose-limiting renal toxicity is common in cisplatin therapy, while hematologic toxicity similar to electrophilic alkylating agents is the major toxicity associated with carboplatin. Both cisplatin and carboplatin have also been associated with gastrointestinal distress, mainly nausea and vomiting, as well as neurotoxic effects.

Since platinum complexes are not extensively metabolized, in vivo, the platinum species present in the body depend upon the reactivity of the complex with water to form hydroxylated and aquated complexes. Further, platinum complexes are largely eliminated from the body through renal excretion, and the acidic conditions present in the kidneys tend to favor the formation of these generally inactive (against neoplasms) and toxic species. In particular, the chloride atoms of cisplatin are readily displaced by hydroxy and aquo moieties under acidic conditions, accounting for the often severe renal toxicity associated with the drug.

Both cisplatin and carboplatin are highly lipophilic compounds, allowing them to readily pass through cell membranes. The hydroxylated and aquated forms are of much lower lipid solubility (particularly at neutral or slightly alkaline pH), which accounts for the general inactivity of these forms of the drug. Further, the elimination of cisplatin takes place much more rapidly than carboplatin, which accounts for the different manifestations of the toxicity.

Other toxic effects associated with platinum complexes are neurotoxicity, ototoxicity (particularly with cisplatin), GI distress, mainly nausea and vomiting, and others.

10. Other Drugs

Similar toxic effects, namely the hematologic toxicities due to bone marrow suppression, GI distress, hypersensitivity, renal toxicity, liver toxicity, mucositis and others, are associated to some degree with most antineoplastic agents. Since the objectives of any cancer therapy program necessarily include prolonging the patient's life, as well as improving the quality of life, manifestations of toxicity are always carefully weighed against the alternatives.

Previously Employed Safety/Protective Measures

With a few exceptions, the efforts at reducing the toxicity of nearly all antineoplastic drugs have mainly involved the use of prophylactic and palliative therapies (such as administering antiemetic drugs to reduce the nausea and vomiting associated with the delivery of many antineoplastic agents) to treat the symptoms of the toxicity of the drugs.

In some cases, other drugs have been coadministered with the antineoplastic agent in an effort to reduce the toxicity thereof. Some classic examples of this type of protective therapy include coadministration of Mesna (2-mercaptoethane sulfonate sodium) to patients receiving oxazaphosphorine chemotherapy. Amifostine is currently administered to patients receiving cisplatin to reduce the severe nephrotoxicity associated with cisplatin. Other protective measures have included transfusions to replenish leukocytes and platelets diminished by the myelosuppression of antineoplastic drugs, and recently, the infusion of colony stimulating factors (CSFs) to stimulate the suppressed bone marrow into producing more of the needed cells. Other prophylactic and preventative measures have been used, normally with little or no success in reducing the toxicity of the antineoplastic drug. In some cases, all therapy had to be ceased due to toxicity of the supposed protective agent.

Mesna use with the oxazaphosphorine drugs ifosfamide and cyclophosphamide has been practiced for several years with some degree of success. U.S. Pat. No. 4,220,660 discloses the usefulness of Mesna for reducing the incidences of bladder toxicity associated with these and other alkylating agents. U.S. Pat. No. 4,218,471 discloses the usefulness of Dimesna (Mesna disulfide) for the same purposes, namely reducing the urotoxic effects of certain electrophilic alkylating agents.

Other commercially known drugs which have been used in conjunction with antineoplastic drugs include leucovorin, which is often used to reduce methotrexate toxicity.

Pharmaceutical Chemistry of Dimesna, Mesna and Derivatives

Dimesna (Disodium-2,2'-dithiobis ethane sulfonate) and derivatives thereof have been found to selectively reduce the toxicity of certain antineoplastic agents, namely certain platinum complex drugs, in vivo. Mesna (Sodium 2-mercaptoethane sulfonate) has been used for years to reduce the acrolein related uroepithelial cell toxicity of ifosfamide and cyclophosphamide, and is approved for such usage in the United States and abroad.

Dimesna is currently starting Phase I clinical trials in the United States as a protective agent for patients receiving cisplatin chemotherapy for their cancer, and has already been proven to be highly effective for such use in pre-clinical animal studies. Dimesna has also been investigated and found to be a highly effective and safe protective agent against certain carboplatin toxicities as well, and is also being investigated as a protective agent with other forms of platinum complexes.

Dimesna is a physiological auto-oxidation dimer of Mesna. However, Dimesna and Mesna differ substantially in physicochemical properties, and have different efficacy and safety profiles.

The pharmaceutical chemistry of the compounds indicates that the terminal sulfhydryl group of Mesna (and to a lesser extent the disulfide linkage in Dimesna) acts as a substitution group for the terminal hydroxy- or aquo- moiety in the toxic metabolites of platinum complexes, and acts as a general free radical scavenger.

Dimesna, unlike Mesna, is postulated to undergo metabolic activation, such as a reduction by glutathione reductase, to exert its biologically efficacious results. Possibly due to its greater molecular stability, and due to the lack of a free thiol moiety, Dimesna also exhibits significantly lower toxicity than Mesna.

Further, neither Dimesna nor Mesna penetrate the cell membranes of many tissues efficiently, with the exception of the cells of the kidney, the GI tract, and perhaps the bone marrow. Therefore, the formula I compounds do not greatly interfere with the cytotoxic action of platinum complexes, although Mesna inactivates platinum complexes to a much higher degree than Dimesna.

Dimesna and its disulfide analogues and derivatives, particularly when administered orally, predominate in the bloodstream in their more stable, less reactive disulfide form, and therefore do not prematurely inactivate the antineoplastic agent to a clinically significant degree, and in fact have been shown to even enhance the antineoplastic activity of some platinum complexes.

Since blood plasma is slightly alkaline (pH ~7.3), the more stable disulfide form is the favored species. The disulfide does not readily react with the terminal chlorine atoms in cisplatin, nor with the cyclobutane dicarboxylato moiety of carboplatin. This allows the antineoplastic drug to perform its intended cytotoxic action on the targeted cancer cells. Postulated and hypothetical mechanisms of action for the platinum complexes are discussed throughout the recent literature.

Further, Dimesna and many of its analogues are very safe for patient administration, even in large doses. In fact, IV Dimesna (4,000 mg/kg, administered once a day for five consecutive days, caused no lethality in rats) is less toxic than orally administered common table salt ($LD_{50}$=3,750 mg/kg in rats). The formula I compounds are also highly water soluble (up to 300 mg/mL), which obviates the need for special formulation with organic solvents or co-solvents, and allows for practical and convenient administration of the protective agent as either a parenteral or an orally administered drug.

As stated above, the reported favored structure in the slightly alkaline environment of blood plasma is Dimesna, while acidic pH tends to favor the reduced species, Mesna. Mesna, due to the presence of the free terminal thiol, is more reactive than Dimesna with regard to substitution for a terminal leaving group.

Prior Art Involving Combination Chemotherapy Using Dimesna

The assignee of this application owns a number of previously filed patent applications, both United States and international, which relate to the use and formulation of Dimesna with various platinum complexes.

The prior patents and patent applications of the assignee identify Dimesna and analogues thereof, and to some extent, analogues of Mesna, as effective protective agents for use with cisplatin and carboplatin when coadministered to patients with cancer. Dose schedules and methods of administration with cisplatin and carboplatin are identified in these references and elsewhere in the art. The use of Mesna as a protective agent has also been well-documented with the oxazaphosphorine antineoplastic agents ifosfamide and cyclophosphamide. Conversely, Mesna has been reported to be incompatible for use with cisplatin.

SUMMARY OF THE INVENTION

This invention relates to the use of Dimesna and analogues and derivatives thereof (hereinafter referred to as "The protective compounds") to reduce the toxicity of certain antineoplastic agents administered to patients as chemotherapy for cancer. The protective compounds are of the following general formula:

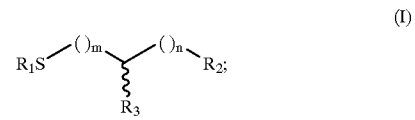

wherein:

$R_1$ is hydrogen, lower alkyl or

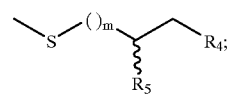

$R_2$ and $R_4$ are each individually $SO_3^-M$, $PO_3^{2-}M_2^{2+}$, or $PO_2S_2^{2+}$;

$R_3$ and $R_5$ are each individually hydrogen, hydroxy or sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof, with the proviso that if the antineoplastic agent is an alkylator of DNA, then $R_1$ is not hydrogen, and if the antineoplastic agent is cisplatin, then $R_1$ is not hydrogen and $R_2$ and $R_4$ are not the same.

Given the pharmacokinetics, as well as the physical, chemical, and biochemical protective properties of the protective compounds, and the proven usefulness of the protective compounds with several structurally different antineoplastic agents, the formula I compounds will be effective in reducing the toxicity of antineoplastic agents which have similar toxic metabolites and/or mechanisms of activation. Particularly, the protective compounds are useful with nearly all of the drugs listed above, whether the combination of the antineoplastic drug and the protective agent is administered concurrently or separately, and regardless of the route of administration to the patient.

As will be described below, the preferred methods of administration include both the coadministration of the protective compound and the desired antineoplastic agent or agents, as well as separate administration thereof. The preferred route of administration of the antineoplastic drug will be the most useful and practical route, most preferably by intravenous injection or infusion, or in some cases oral, while the administration of the formula I compound can be either oral or parenteral, irrespective of the method of delivery of the antineoplastic drug. Preferred doses of each antineoplastic agent and a protective compound are also set forth below.

Accordingly, it is a principal object of this invention to provide for a novel method of treating cancer patients, by administering an effective amount of i) an antineoplastic agent; and ii) a formula I protective compound as described herein.

Another object of this invention is to provide for a method of reducing the toxicity, in vivo, of an antineoplastic agent when administered to a patient as cancer chemotherapy.

Another object of this invention is to provide for a improved and safer methods of treating patients with cancer.

Other objects will become apparent upon a reading of the following description.

DESCRIPTION OF THE PREFERRED EMBODIMENTS

The preferred embodiments herein described are not intended to be exhaustive or to limit the scope of the invention to the precise forms disclosed. They are chosen and described to best explain the principles of the invention and its application and practical use to allow others skilled in the art to comprehend its teachings.

The primary objectives of any chemotherapeutic regimen utilized in the treatment of patients with cancer must necessarily be 1) to cure the patient by killing off all the neoplastic cells; 2) to induce a remission of the cancer by halting the growth and spread of the neoplasm; 3) to provide palliative treatment, improving the quality of life for patients whose neoplasms cannot be controlled; and 4) to achieve the above with the least amount of risk to the patient's overall health and quality of life.

This invention relates to formulations and methods of use which are designed to achieve the above goals of cancer chemotherapy. It is well-known that the difficulties in obtaining positive results with many chemotherapeutic regimens involve the toxic side effects associated with nearly all of the antineoplastic drugs currently in use. Often, the dosage of the antineoplastic drug(s) being administered to the patient must be reduced or even discontinued to reduce the toxic effects of the drug on the patient's normal, healthy cells. Dose lowering or discontinuance most obviously has a direct negative affect on the success or failure of the treatment.

This invention provides for formulations of compounds having the following formula I in combination with one or more antineoplastic agents:

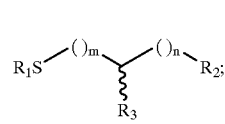

(I)

wherein:

$R_1$ is hydrogen, lower alkyl or

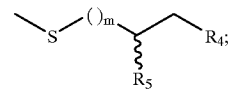

$R_2$ and $R_4$ are each individually $SO_3^- M^+$, $PO_3^{2-} M_2^{2+}$, or $PO_2 S^{2-} M_2^{2+}$;

$R_3$ and $R_5$ are each individually hydrogen, hydroxy or sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof, with the proviso that if the antineoplastic agent is an alkylator of DNA, then $R_1$ is not hydrogen, and if the antineoplastic agent is cisplatin, then $R^1$ is not hydrogen and $R_2$ and $R_4$ are not the same.

As defined above, "antineoplastic agent" means a compound which is administered to a patient as a therapeutic agent for the purpose of treating a neoplastic disease. Antineoplastic agents with which the formula I compounds may be formulated for use include the following:

1. Fluoropyrimidines
2. Pyrimidine Nucleosides
3. Purines
4. Platinum Analogues
5. Anthracyclines/Anthracenediones
6. Podophyllotoxins
7. Camptothecins
8. Hormones and Hormonal Analogues
9. Vinca Alkaloids
10. Taxanes
11. Antihormonals
12. Antifolates
13. Antimicrotubule Agents
14. Alkylating Agents (Classical and Non-Classical)
15. Antimetabolites
16. Antibiotics
17. Topoisomerase Inhibitors
18. Miscellaneous Cytotoxic Agents

Antineoplastic Agent Structures
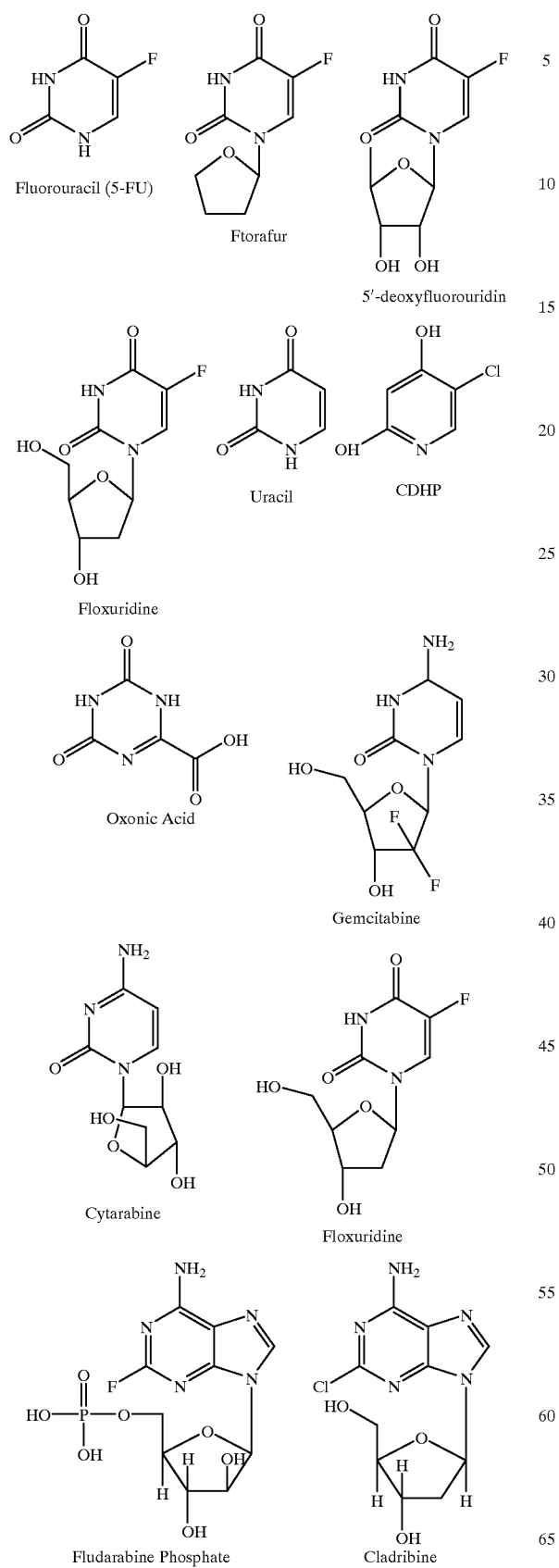
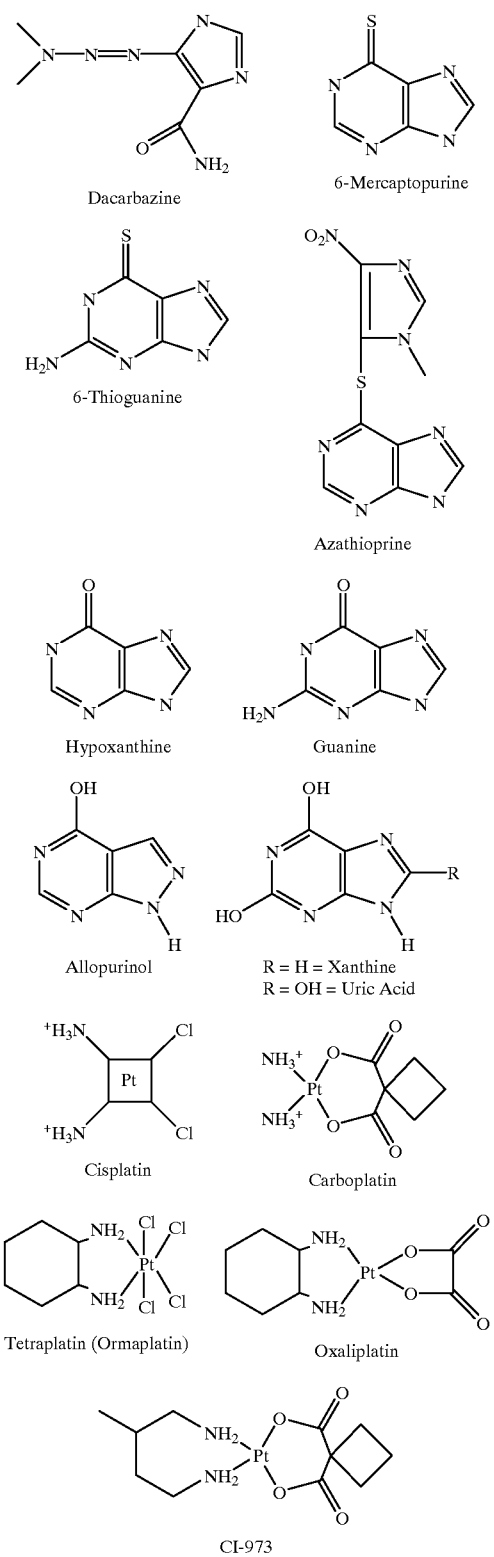

-continued
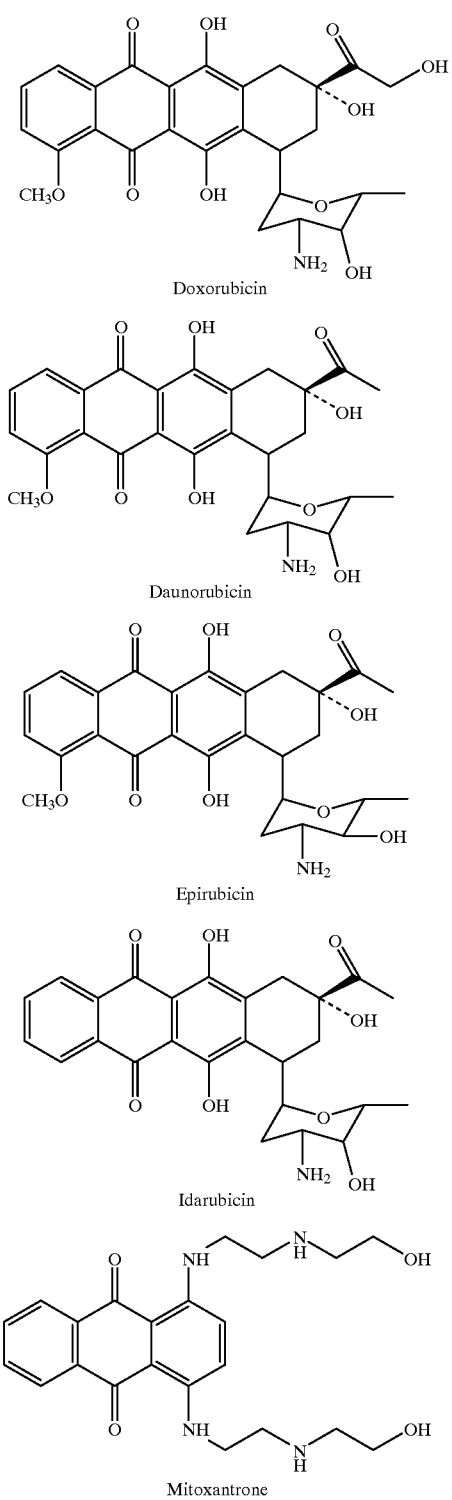
Doxorubicin
Daunorubicin
Epirubicin
Idarubicin
Mitoxantrone
-continued
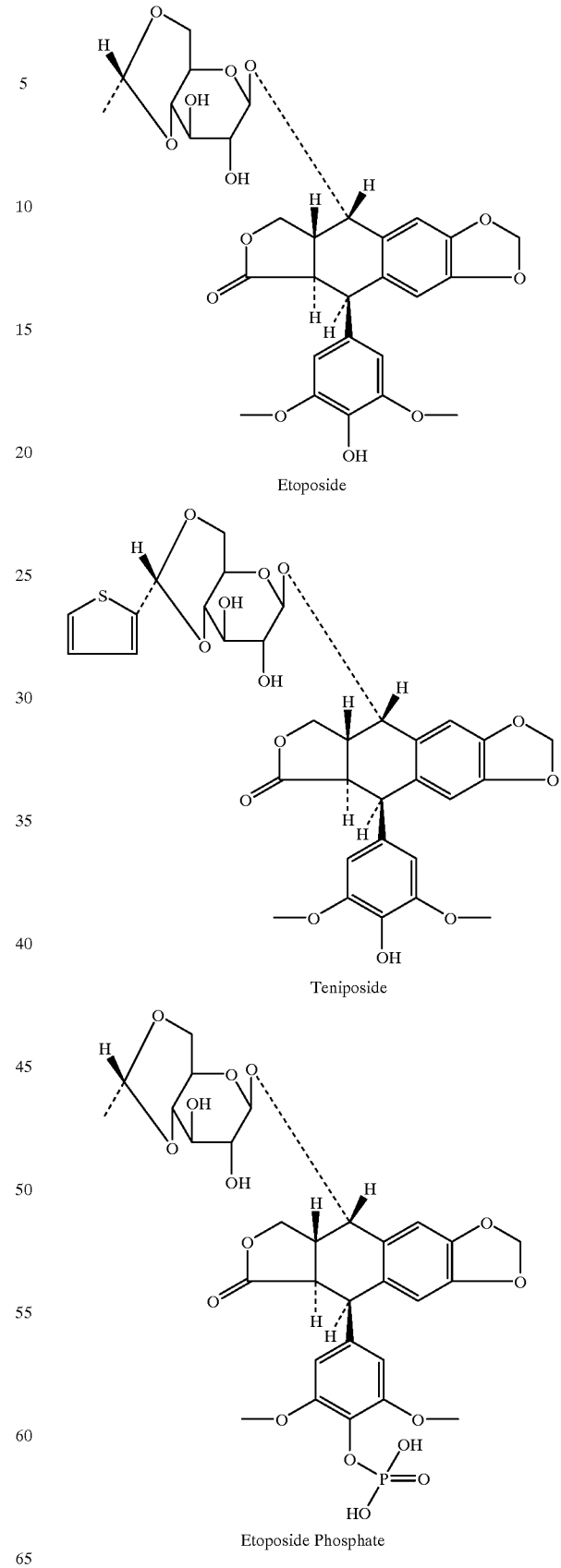
Etoposide
Teniposide
Etoposide Phosphate

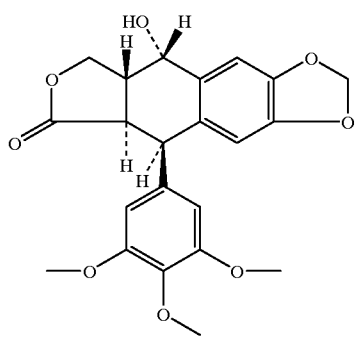
Podophyllotoxin
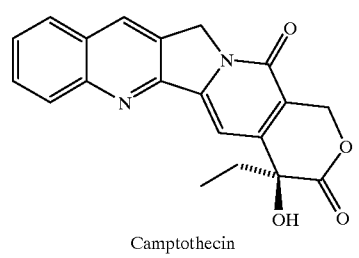
Camptothecin
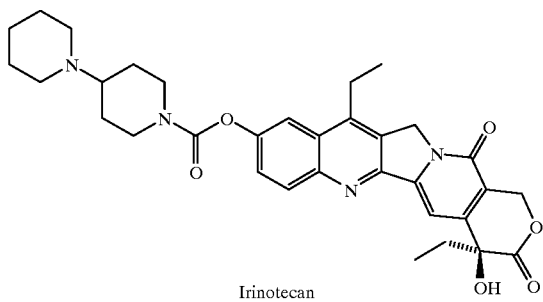
Irinotecan
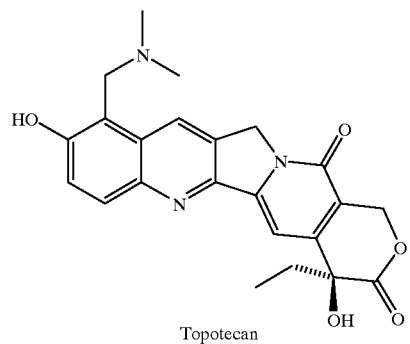
Topotecan
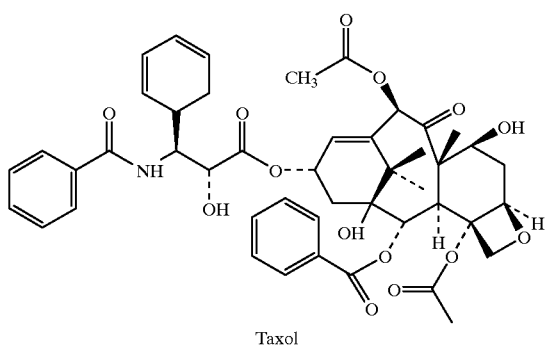
Taxol
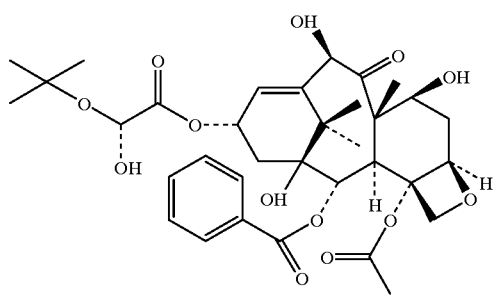
Taxotere
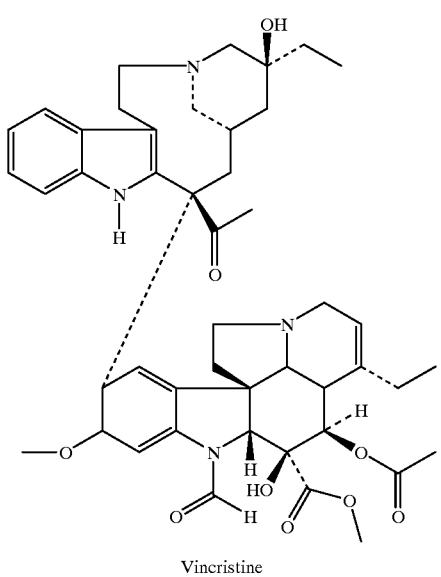
Vincristine
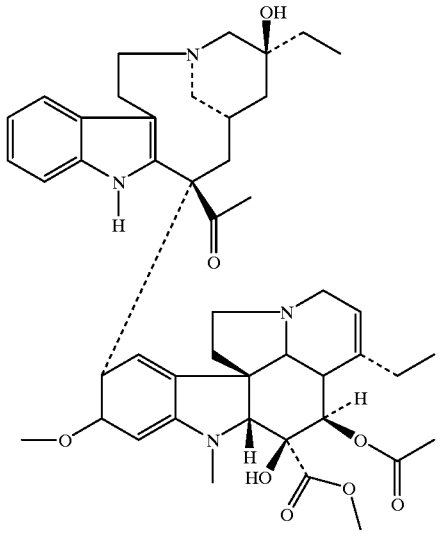
Vinblastine

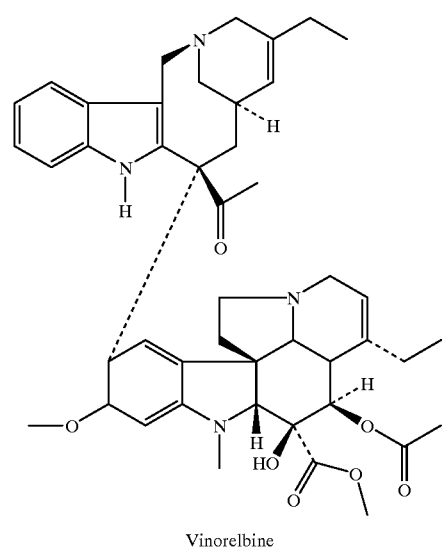
Vinorelbine
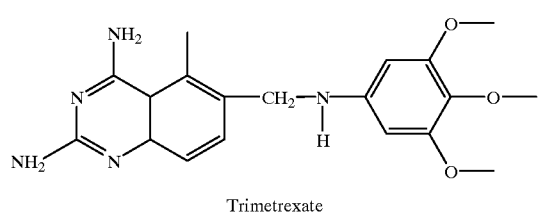
R = H Aminopterin
R = CH₃ Methoptrexate
10-ethyl-10-deaza aminopterin (EDAM)
γ-methylene-10-deaza aminopterin (MDAM)
5, 10-dideaza tetrahydrofolate
Trimetrexate
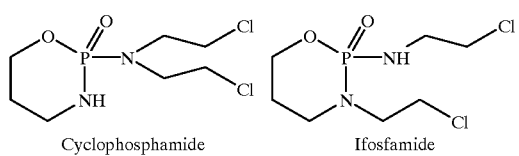
Cyclophosphamide    Ifosfamide
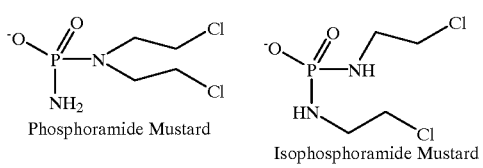
Phosphoramide Mustard    Isophosphoramide Mustard
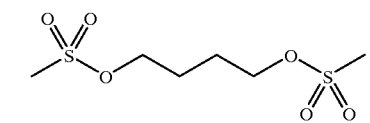
Busulfan
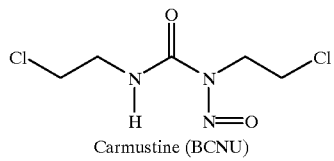
Carmustine (BCNU)
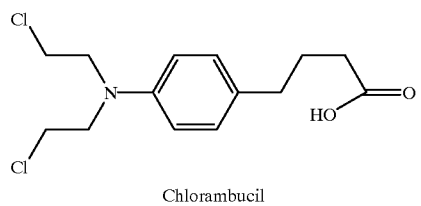
Chlorambucil
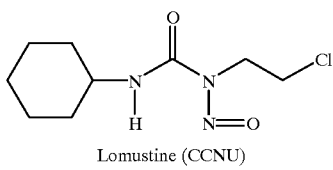
Lomustine (CCNU)
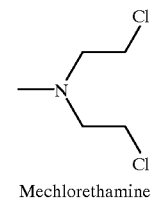
Mechlorethamine
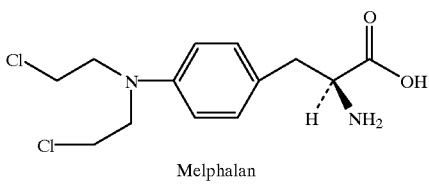
Melphalan
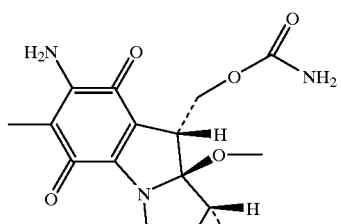
Mitomycin
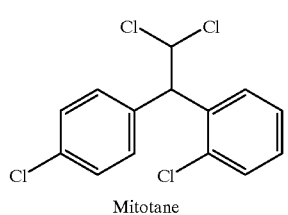
Mitotane

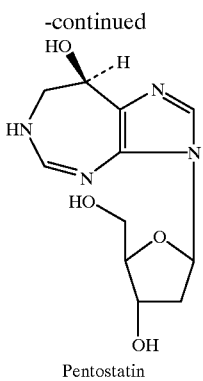

Pentostatin

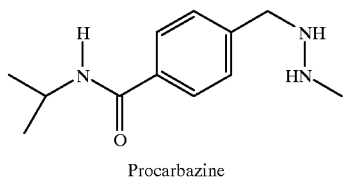

Procarbazine

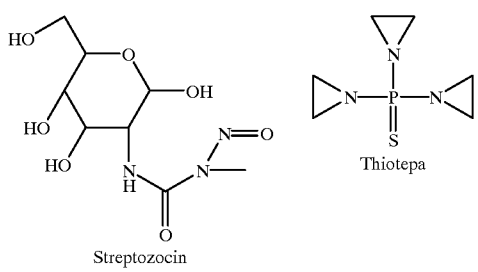

Streptozocin

Thiotepa

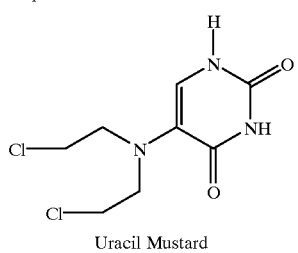

Uracil Mustard

It should be noted that the above classifications include antineoplastic agents which may be classified in two or more categories, with some agents actually being classifiable in three or even four of the above categories. The listings provided above are for guidance only, and should not be construed as limiting or all-inclusive.

The formula I compounds are useful in reducing the common, major toxicities of a large number of antineoplastic drugs. The formula I compounds will also no doubt prove useful in reducing the toxicity of other drugs as well, particularly those drugs which generate similar toxic species. In general, the formula I compounds are postulated to be useful in reducing the toxicity of any antineoplastic agent which includes one or more hydroxy, aquo, aziridinium, or other moieties which are substitutable by a strong nucleophile, in vivo.

Formulations of the antineoplastic agent(s) and the formula I compounds are one of the preferred embodiments of this invention. In this embodiment, the antineoplastic agent and the formula I compound may be combined in a single solution, suspension, or other dosable form and packaged for later delivery to the patient.

A second embodiment of this invention relates to the formulation of the formula I compound with a suitable solvent (parenteral formulations) or as a pure drug or formulated with a carrier (oral formulations). The antineoplastic agent is packaged in a separate formulation, distinct from the formula I formulation, with the two formulations adapted to be reconstituted and delivered to the patient at the same time as the antineoplastic agent. Administration of an effective amount of the formula I compound in all embodiments serves to reduce the undesired toxicity of the antineoplastic agent.

A third embodiment of the invention relates to the administration of the formula I compound separately from the antineoplastic agent. Delivery of the formula I compound is effected prior to the administration of the antineoplastic agent, to reduce the undesired toxicity of the antineoplastic agent.

A fourth embodiment of the invention relates to the delivery of the formula I compound after the administration of the antineoplastic agent, to reduce the toxicity of the antineoplastic agent.

A fifth embodiment of the invention relates to the intermittent administration of the formula I compounds after administration of the antineoplastic agent. This route of delivery may be combined with any of the other schedules set forth for the initial administration with the formula I compound.

In all embodiments, the term "effective amount" is understood as a medical art term, that is, the dose schedule and route of administration of the drug which gives the best therapeutic value and convenience to the patient. With regard to antineoplastic drugs, and the reduction of toxicity by administration the formula I compounds, an "effective amount" of formula I compound is defined as the amount of drug which reduces the manifestation of toxic side effects of the antineoplastic drug. In most cases, the range of the effective amount is estimated by the clinical oncologist using the dose schedule, pharmacokinetic properties, and the patient's weight and body surface area, and adjusting the dose and timing such that the peak concentrations of the protective agent and the peak concentration of the toxic species of the antineoplastic agent have the greatest amount of overlap.

Thus, the timing of administration of the formula I compound with respect to the timing of the administration of the antineoplastic agent will vary according to the dose, schedule, route of administration, and individual pharmacokinetics of the antineoplastic agent being used. The most desired dose ratios, timing, and total amounts of drugs administered, will depend upon the type of antineoplastic agent being administered, the toxicities associated with that agent, the overall condition of the patient and the susceptibility of the patient to the antineoplastic drug's side effects, the efficacy of the formula I compound with respect to detoxification of the antineoplastic agent, and other factors.

The administration of an effective amount of a formula I compound reduces the toxicity of the antineoplastic agent (s). The dosage and timing of administration of the formula I compounds is always designed to maximize patient safety throughout the course of the chemotherapeutic regimen. The effectiveness of the formula I compound in achieving the objectives of toxicity reduction and patient safety will depend to some extent on the dosing schedules, and some typical schedules and dosage ratios are described for each antineoplastic agent and class of antineoplastic agent with which the formula I compounds may be administered.

Co-formulation of Antineoplastic Agents and Formula I Compounds

The first embodiment of the invention involves the combination of the antineoplastic agent and the formula I compound in the same pharmaceutical formulation. The main advantage to a co-formulation of the antineoplastic agent and the formula I compound is the ease and convenience of reconstitution by the pharmacist and the nurse, and the ease of administration to the patient. Disadvantages include the potential for premature reactions of the formula I compound and the antineoplastic agent which could result in premature inactivation of the antineoplastic agent, and failure to achieve toxicity reduction due to different drug cycle times in the body. If the possibility of premature inactivation of the antineoplastic agent is a concern, then the two compounds should be formulated separately for administration to the patient.

A typical example of safeguards used to prevent premature reaction of the formulation components is taken from the prior art which involves the combination of cisplatin and Dimesna. In order to prevent the removal of the chlorine groups in favor of the disulfide or sulfhydryl moieties of the formula I compound, the formulation is spiked with additional chloride ions, such as are found in a 0.9% sodium chloride solution. Other examples of safeguards to protect the integrity of the formulation will be apparent to those skilled in the art.

A co-formulation of the formula I compound and the antineoplastic agent can take on any of several forms, dependent upon the intended delivery route of the formulation. For purposes of this invention, parenteral, topical and oral formulations will be described.

In a typical parenteral formulation, the two compounds must be dissolved or suspended in a suitable solvent delivery vehicle.

Pharmaceutically acceptable solvents are well-known in the art, and by ascertaining the solubility of the formula I compound and the antineoplastic agent in various pharmaceutically acceptable solvents, a formulation expert can determine the maximum concentration of both compounds in a preferred formulation. One or more co-solvents can be used if necessary to ensure complete dissolution of the compounds if the desired form of delivery is a solution. Excipients may be added to the solution or suspension to provide for pharmaceutical elegance of the formulation.

The most preferred solvent in many formulations, due to its relative lack of toxicity and ease of delivery, is water. Since the solubility of most formula I compounds is at least 300 mg/mL, the water solubility of the antineoplastic agent will determine the usefulness of water as the primary solvent. If the desired dosage of the antineoplastic agent and the formula I compound can be fully dissolved in water, such as in the case of many antineoplastic agents administered as salts of the free base, as well as many of the alkylating agents, platinum complexes, nucleosides, purines, and others, then water will be the preferred solvent. As stated above, any chances of premature reaction of the formulation ingredients must be safeguarded against. If delivery of a suspension is preferred, the solubility of the compounds in the solvent(s) important, but not as critical as the solubility when delivering a solution.

In the event an oral formulation is desired, a suitable carrier is necessary. Preferred forms of oral delivery vehicles include filled capsules, pills, caplets, oral solutions or suspensions, tablets, and other common oral dosage forms. Filled capsules may contain either a solution or a suspension of the formula I compound with or without the antineoplastic agent. The above disclosure regarding solubility and choice of solvents in parenteral formulations applies also to the oral formulations.

In the event of topical formulations, the preferred forms include lotions, creams, solutions, suspensions, or other forms which can be applied topically. Although only Fluorouridine (5-FU) is currently approved in the United States for use as a topically applied antineoplastic agent, formulations of certain antineoplastic agents and a formula I compound would likely be useful against some skin cancers.

The preferred dosage of many antineoplastic agents is a variable, and is based upon the type of tumor, other drugs included in the therapeutic regimen, height of the patient, weight of the patient, age of the patient, and in some cases, the gender of the patient. Since the efficacy of the formula I compounds has some dependence on the amounts of both compounds delivered, the preferred formulations are described as weight-to-weight ratios of the formula I compound and the antineoplastic agent. Preferred solvents are also described for each formulation.

TABLE 2

| Drug | Route | w/w Ratio (drug:formula I) |
|---|---|---|
| Bleomycin | Parenteral | 1:5–1:4000 |
| Busulfan | Oral or Parenteral | 1:5–1:5000 |
| Carboplatin | Parenteral | 1:5–1:4000 |
| Carmustine | Parenteral | 1:5–1:4000 |
| Chlorambucil | Oral | 1:5–1:4000 |
| Cisplatin | Parenteral | 1:5–1:4000 |
| Cladribine | Parenteral | 1:5–1:5000 |
| Cyclophosphamide | Oral or Parenteral | 1:5–1:5000 |
| Cytarabine | Parenteral or Subcutaneous | 1:5–1:5000 |
| Dacarbazine | Parenteral | 1:5–1:5000 |
| Dactinomycin | Parenteral | 1:5–1:4000 |
| Daunorubicin | Parenteral | 1:5–1:4000 |
| Docetaxel | Parenteral | 1:5–1:4000 |
| Doxorubicin | Parenteral | 1:5–1:4000 |
| Etoposide | Oral or Parenteral | 1:5–1:4000 |
| Floxuridine | Parenteral | 1:5–1:5000 |
| Fludarabine | Parenteral | 1:5–1:5000 |
| Fluorouracil | Parenteral or Topical | 1:5–1:5000 |
| Gemcitabine | Parenteral | 1:4–1:4000 |
| Hydroxyurea | Oral | 1:5–1:4000 |
| Ifosfamide | Parenteral | 1:5–1:5000 |
| Irinotecan | Parenteral | 1:5–1:5000 |
| Lomustine | Oral | 1:5–1:5000 |
| Mechlorethamine | Parenteral | 1:5–1:4000 |
| Melphalan | Oral or Parenteral | 1:5–1:5000 |
| Mercaptopurine | Oral | 1:5–1:5000 |
| Methotrexate | Parenteral or Oral | 1:5–1:5000 |
| Mithramycin | Parenteral | 1:5–1:4000 |
| Mitomycin | Parenteral | 1:5–1:4000 |
| Mitotane | Oral | 1:5–1:4000 |
| Mitoxantrone | Parenteral | 1:5–1:4000 |
| Paclitaxel | Parenteral | 1:4–1:4000 |
| Pentostatin | Parenteral | 1:5–1:4000 |
| Procarbazine | Oral | 1:5–1:5000 |
| Streptozocin | Parenteral | 1:5–1:5000 |
| Teniposide | Parenteral | 1:5–1:4000 |
| Thioguanine | Oral | 1:5–1:5000 |
| Thiotepa | Parenteral | 1:5–1:5000 |
| Uracil Mustard | Oral | 1:5–1:5000 |
| Vinblastine | Parenteral | 1:5–1:5000 |
| Vincristine | Parenteral | 1:5–1:5000 |
| Vinorelbine | Parenteral | 1:5–1:5000 |
| Azathioprene | Parenteral | 1:5–1:5000 |
| Epirubicin | Parenteral | 1:5–1:4000 |
| Idarubicin | Parenteral | 1:5–1:4000 |
| EDAM | Parenteral or Oral | 1:5–1:5000 |

TABLE 2-continued

| Drug | Route | w/w Ratio (drug:formula I) |
|---|---|---|
| MDAM | Parenteral or Oral | 1:5–1:5000 |
| Topotecan | Parenteral or Oral | 1:5–1:5000 |
| Ftorafur | Parenteral | 1:5–1:4000 |
| UFT | Oral or Parenteral | 1:5–1:5000 |
| S-1 | Oral or Parenteral | 1:5–1:5000 |
| Oxalaplatin | Parenteral | 1:5–1:5000 |
| Temozolomide | Parenteral | 1:5–1:5000 |
| Hexamethylmelamine | Parenteral | 1:5–1:5000 |
| Tetraplatin | Parenteral or Oral | 1:5–1:5000 |
| Lobaplatin | Parenteral | 1:5–1:5000 |
| CI-973 | Parenteral | 1:5–1:5000 |
| JM216 | Oral or Parenteral | 1:5–1:5000 |
| m-AMSA | Oral or Parenteral | 1:5–1:4000 |
| Elliptinium | Parenteral | 1:5–1:4000 |
| CI-921 | Parenteral | 1:5–1:4000 |
| 9-Amino CPT | Oral or Parenteral | 1:5–1:4000 |
| Pyrazoloacridine | Parenteral | 1:5–1:4000 |
| CI-980 | Parenteral | 1:5–1:4000 |
| Azacytidine | Parenteral | 1:5–1:4000 |
| AZQ | Parenteral | 1:5–1:4000 |

Table 1 depicts the preferred range for dose ratios of the formula I compound with a variety of antineoplastic agents. The most preferred dosage ratio will vary depending upon a number of factors in each case, with the principal objective being the safety of the patient.

Steps are also taken to preserve the integrity of the formulation, to prevent the premature reaction of the formula I compound with the antineoplastic agent. If there is a danger of the compounds reacting in the formulation, regardless of precautions taken, then they are formulated separately for administration.

Formulations of the Formula I Compounds

The formula I compounds may be formulated for administration apart from the administration of the antineoplastic agent. The preferred solvent for making parenteral formulations of the to formula I compounds is water. Oral formulations also use water as the preferred primary solvent, if any solvent is used.

The concentration of the formula I compound in any given parenteral formulation is determined by the final desired form. If the final form is a solution, the upper limit of the concentration of the formula I compound is its maximum solubility in the solvent or solvents selected. If the final form is a suspension, the concentration may be higher.

For oral dosage forms, the total amount of formula I compound present in the dose is preferably an amount which will allow a recommended dose to be conveniently administered. The primary factor in determining the amount of formula I compound contained in oral doses is the required size of the delivery vehicle.

All parenteral and oral formulations of the formula I compounds are designed to be administered to a patient according to the methods taught by this invention. General examples of parenteral and oral formulations of the formula I compounds are depicted below. The most preferred formula I compounds are Dimesna, the disphosphonate analogue of Dimesna (dimephos), the heterodimer of Mesna, where $R^2$ is sulfonate, $R^4$ is phosphonate (mesnaphos), S-methyl Mesna, and those analogues where one or both of $R^3$ and $R^5$ are hydroxy and m and n are at least 1 (hydroxymesna). All of these most preferred compounds have a water solubility of at least 200 mg/mL, with the hydroxy derivatives having the greatest water solubility.

Formulations of the formula I compounds may also include pharmaceutically acceptable excipients, carriers and/or diluents. The composition and amount of each additional material in the formulation will depend upon the desired route of delivery, speed of administration, the timing of drug delivery after administration of the formulation, final desired concentration, and other factors. One preferred excipient which will be included in many formulations is a pH adjustment compound, which is typically either a pharmaceutically acceptable acid or base. Most preferred formulations of the formula I compounds are depicted in the specific examples, infra.

Use of the Formula I Compounds To Reduce Toxicity

This invention also relates to the use of the formula I compounds to reduce the undesirable toxic side effects of many antineoplastic drugs. Most of the undesired toxic effects of the antineoplastic agents are described above.

There are several varying mechanisms, described above, by which most antineoplastic agents exert both the desired cytotoxic effects and the undesirable toxic effects on normal healthy cells. Administration of a formula I compound in conjunction with one of these antineoplastic agents serves to reduce, and in some cases eliminate the toxic side effects associated with the antineoplastic agent. Also, due to the pharmacologic properties of the formula I compounds, the reduction of undesired toxicity is not accompanied by a similar fall-off in activity of the antineoplastic agent against targeted neoplastic cells.

To ensure maximum effect, the formula I compound should be administered such that a suitable concentration of the formula I compound is present in the body to react with the antineoplastic agent and metabolites thereof. Preferred timing of the dosage of the formula I compound will depend upon the pharmacologic properties of the particular antineoplastic agent, generally from about one minute prior to the administration of the antineoplastic agent to about one hour prior to such administration. The most preferred initial route of administration of the formula I compound at this time is by a single IV push, which is administered between fifteen and thirty minutes prior to the start of administration of the antineoplastic agent.

The preferred ratios of administration are depicted in Table 1 above. These ratios are applicable for all routes of initial administration of the formula I compound and the antineoplastic agent, whether the two are administered simultaneously or staggered, and whether the two are administered in the same or separate formulations.

In the cases where the reduction of toxicity mechanism of action is known or postulated, the formula I compounds are postulated to reduce the undesired side effect toxicity of the antineoplastic agent by displacing terminal leaving groups thereon. Particularly susceptible leaving groups include those groups subject to displacement by a moderate to strong nucleophile, in the formula I compounds represented by the sulfhydryl (and to a lesser extent, the disulfide) moiety.

The leaving groups in many instances are hydroxy moieties, aquo moieties, aziridinium ions, and other displaceable free radical type moieties. In many cases, the antineoplastic agent metabolite which contains these moieties has little or no antineoplastic activity, but manifests undesired toxic side effects to healthy cells. Displacement of the terminal leaving group in such cases by the sulfhydryl or disulfide of the formula I compound generates a non-toxic thioether moiety, one which is rapidly eliminated from the body.

Another embodiment involves the administration of the formula I compounds at intermittent times after the administration of the antineoplastic agent. This type of administration is seen to be particularly effective when the antineoplastic agent has a prolonged and/or multiphasic half-life. Since the formula I compounds are eliminated rapidly from the body ($t_{1/2} \leq 90$ minutes), administration of the formula I compound at predetermined intervals following administration of the antineoplastic agent can provide long term protection against later occurring side effects. This prolonged protection can be extremely beneficial in the case of antineoplastic agents such as the Anthracyclines, Platinum Analogues, Vinca Alkaloids, Taxanes, and other agents which remain in the body in appreciable quantities for extended periods (e.g. $t_{1/2} > 24$ hours).

Combination chemotherapy, where two or more antineoplastic agents are administered simultaneously or near simultaneously, presents special considerations in administration of the formula I compounds. Due to the extremely low toxicity of the formula I compounds, large doses, often exceeding 10 grams or more, can be given to the patient as a single dose. Reduction of side effects of combination antineoplastic agents is postulated to be dependent upon the pharmacokinetics of the individual agents, and the electrophilic affinity of the displaceable leaving groups of each agent.

The most critical factor of delivering an effective amount of formula I compound to the patient is the maximization of the peak plasma concentration of the protective agent with the peak concentration of the toxic species of the antineoplastic agent. The curve is actually a time versus concentration graph which depicts the concentration of active drug in the bloodstream as a function of time.

Typical time/concentration curves have been generated for each of the commercial and many other antineoplastic drugs so that estimates of the effective amount and timing of administration of each agent can be ascertained. This research enables clinical oncologists to determine better courses of therapy for individual patients. In combination chemotherapy in particular, it is often desirable to select agents which have different time/concentration curves, to ensure that the maximum effect of each agent is achieved, and to correspondingly reduce the risk of cumulative drug toxicity. The accepted therapeutic value of a drug in the oncology field is referred to as the area under the curve (AUC), which refers to the space occupied beneath the time/concentration curve. More area present beneath this curve is equated with greater therapeutic value from a pharmacokinetic standpoint.

The objective in administering the formula I compounds to the patient is to match as closely as possible the peak concentrations of the toxic species of the antineoplastic agent(s) and the formula I compounds. By closely matching peak concentrations of the antineoplastic agent and the formula I compound, maximum detoxification can be attained. Since the pharmacokinetics of all the commercially available antineoplastic agents are known or constitute predictable values, the clinical oncologist can tailor the timing and dosage of the formula I compound to achieve the optimal result.

Dose ratio is also an important factor for the oncologist to evaluate in administering an effective amount of the formula I compound. The dose ratios illustrated above in Table 2 are intended to present guidelines to the practitioner, with actual dose ratios and dose amounts set on a case-by-case basis as the patient's treatment progresses.

Individual treatment regimens, while initially following the prescribed dosing timing and amounts, are often adjusted by the oncologist to achieve the greatest therapeutic results with concomitantly low risk due to toxic side effects of the antineoplastic agent. In many cases, dose reduction of the antineoplastic agent can be avoided, with a change in timing and/or an increase in dosage of the protective agent. By allowing the patient to continue to receive high therapeutic doses of the antineoplastic agent, the probability of successful treatment is increased.

In one of its preferred embodiments, this invention involves the preparation and administration of a sterile, aqueous formulation of cis-diammine dichloro platinum with 2,2'-dithio-bis-ethane sulfonate in the same formulation.

SPECIFIC EXAMPLES

The following examples illustrate selected modes for carrying out the claimed invention and are not meant to be construed as limiting the specification and claims in any way.

Example 1

Preparation of 2,2'-Dithio-bis-ethane Sulfonate 2,2'-Dithio-bis-ethane sulfonate is prepared by oxidizing 2-mercapto ethane sulfonate in water with equimolar amount of iodine as previously reported by Lamaire and Reiger (Lamaire and Reiger, *J. Org. Chem.*, 26, 1330–1, 1961).

Example 2

Stability of 2,2'-Dithio-bis-ethane Sulfonate

The stability of 2,2'-dithio-bis-ethane sulfonate at room temperature was determined at pH ranges of 1.5 to 9.0. 2,2'-Dithio-bis-ethane sulfonate, as produced by the method described above, was found to be very stable in the pH range of 1.5–9.0.

The following experiment was performed to determine the stability of 2,2'-dithio-bis-ethane sulfonate in acidic and basic aqueous media. In a typical experiment, 50 mg of 2,2'-dithio-bis-ethane sulfonate (as produced by using the above described method) was dissolved in one ml of water and the pH was adjusted to 1.5, 2.0, 3.0, 4.0, 5.0 and 6.0 by adding 1 N hydrochloric acid in water or the pH was adjusted to 8.0 and 9.0 by adding 1 N sodium hydroxide in water. The reaction mixture was stirred for 24 hours at room temperature, the water was removed at reduced pressure, dissolved in spectral grade $D_2O$, and the proton NMR spectrum was recorded. One peak corresponding to the starting material was observed on the NMR spectra; no additional peaks were observed.

The stability of 2,2'-dithio-bis-ethane sulfonate at pH 1.5 was further studied by heating the reaction mixture to 100 degrees Celsius for 10 minutes. No change in the proton spectrum was observed by heating the 2,2'-dithio-bis-ethane sulfonate (pH 1.5). These data indicate that 2,2'-dithio-bis-ethane sulfonate is stable in aqueous solutions at pH values from 1.5 to 9.0.

Example 3

Method #1 to Produce a Sterile Solution Containing Cisplatin and 2,2'-Dithio-bis-ethane Sulfonate This example is designed to detail one method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus minus 1%.

Step 1. U.S.P. grade of sodium chloride (NaCl; purchased from VWR Scientific) is dissolved in sterile, injectable water to a final concentration of 0.9% NaCl by weight of water. A suitable amount of pure hydrochloric acid (HCl, 99.999%; purchased from Aldrich Chemical Company) is added to the sterile, injectable 0.9% sodium chloride solution in order to obtain a final pH in the range of approximately 2.0 to 6.0.

Step 2. One part by weight of pure, cisplatin (99.999%, purchased from Aldrich Chemical Company) is added to the admixture of Step 1. The cisplatin is allowed to completely dissolve by agitation (1500–2500 rpm) at room temperature, for approximately 60 to 90 minutes.

Step 3. Then, 15 parts by weight of disodium 2,2'-dithio-bis-ethane sulfonate (as produced above in Example 1) is added the mixture of Step 2. This mixture is agitated until complete dissolution and the final pH is adjusted to a pH ranging between approximately pH 2.0 and pH 6.0 by adding pure hydrochloric acid (99.999%, purchased from Aldrich Chemical Company).

Step 4. The solution of Step 3 is sterilized via filtration through a sterile 0.22 micron filter (obtained from VWR Scientific).

Step 5. The sterile solution of Step 4 is stored in sterile injection vials wherein each vial contains approximately 0.9 mg of cisplatin and 14.3 mg of 2,2'-dithio-bis-ethane sulfonate per ml of injection solution.

Example 4

Method #2 to Produce a Sterile Solution Containing Cisplatin and 2,2'-Dithio-bis-ethane Sulfonate This example is designed to detail another method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus minus 1%.

Step 1. U.S.P. grade of sodium chloride (NaCl; purchased from VWR Scientific) is dissolved in sterile, injectable water to a final concentration of 0.9% NaCl by weight of water.

Step 2. Disodium 2,2'-dithio-bis-ethane sulfonate (as produced above in Example 1; fifteen (15) parts by weight) is added to the sterile, injectable 0.9% NaCl solution from Step 1. The 2,2'-dithio-bis-ethane sulfonate is allowed to completely dissolve by agitation (1500–2500 rpm) at room temperature. This should take approximately 5–10 minutes at room temperature. The pH of the 2,2'-dithio-bis-ethane sulfonate solution is adjusted to a pH ranging between approximately pH 2.0 and pH 6.0 by adding pure (99.999% purity) hydrochloric acid.

Step 3. Pure (99.999% purity) cisplatin is added (1 part by weight) to the solution of Step 2. This mixture is agitated until complete dissolution and the final pH is adjusted to a pH ranging between approximately pH 2.0 and pH 6.0 by adding pure (99.999% purity) hydrochloric acid.

Step 4. The solution of Step 3 is sterilized via filtration through a sterile 0.22 micron filter (obtained from VWR Scientific).

Step 5. The sterile solution of Step 4 is stored in sterile injection vials wherein each vial contains approximately 1.0 mg of cisplatin and 14.3 mg of 2,2'-dithio-bis-ethane sulfonate per ml of injection solution.

Example 5

Method #3 to Produce a Sterile Solution Containing Cisplatin and 2,2'-Dithio-bis-ethane Sulfonate This example is designed to detail another method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus minus 1%.

Step 1. A suitable amount of pure, disodium 2,2'-dithio-bis-ethane sulfonate (as produced in Example 1) is dissolved in sterile, injectable water to a concentration of 15.0 mg/ml.

Step 2. U.S.P. grade sodium chloride crystals (NaCl; purchased from VWR Scientific) is added to the solution of Step 1 such that the final concentration of NaCl is 0.9% by weight of water.

Step 3. The pH of the 2,2'-dithio-bis-ethane sulfonate—NaCl solution of Step 2 is adjusted to range between approximately pH 2.0 and pH 6.0 by the addition of pure (99.999% purity), hydrochloric acid (purchased from Aldrich Chemical Company).

Step 4. An amount of pure (99.999% purity) cisplatin is added to the solution of Step 3 such that the final concentration is approximately 1.0 mg/ml cisplatin.

Step 5. The solution of Step 4 is sterilized via filtration through a sterile 0.22 micron filter.

Step 6. The sterile solution of Step 5 is store in sterile injection vials wherein each vial contains approximately 1.0 mg of cisplatin and 14.3 mg of 2,2'-dithio-bis-ethane sulfonate per ml of injection solution.

Example 6

Method #4 to Produce a Sterile Solution Containing Cisplatin and 2,2'-Dithio-bis-ethane Sulfonate This example is designed to detail another method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. U.S.P. grade sodium chloride (NaCl; purchased from VWR Scientific) dissolved in sterile, injectable water to a final concentration of 0.9% NaCl by weight of water.

Step 2. The pH of this NaCl solution is brought to approximately 2.0 to 6.0 by the addition of 99.999% pure hydrochloric acid (purchased from Aldrich Chemical Company).

Step 3. Suitable amount of pure (99.999% purity) cisplatin (obtained from Aldrich Chemical Company) is added to the solution obtained in Step 2 and allowed to dissolve completely by agitation (1500–2500 rpm) for approximately 60 to 90 minutes at room temperature.

Step 4. Then, 30 parts by weight of disodium 2,2'-dithio-bis-ethane sulfonate (as produced in Example 1) is added to the solution Step 3. The 2,2'-dithio-bis-ethane sulfonate—cisplatin mixture is allowed to completely dissolve with agitation at room temperature.

Step 5. The pH of the disodium 2,2'-dithio-bis-ethane sulfonate—cisplatin solution is adjusted to a final pH ranging between approximately 2.0 and 6.0 by the addition of pure (99.999% purity) hydrochloric acid (obtained from Aldrich Chemical Company).

Step 6. The solution of Step 5 is sterilized via filtration through a sterile 0.22 micron filter (obtained from VWR Scientific) Step 7. The sterile solution of Step 6 is stored in sterile injection vials wherein each vial contains 0.5 mg of cisplatin and 12.9 mg of 2,2'-dithio-bis-ethane sulfonate per ml of injection solution.

Example 7

Method #5 to Produce a Sterile Solution Containing Cisplatin and 2,2'-Dithio-bis-ethane Sulfonate This example is designed to detail another method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. U.S.P. grade sodium chloride (NaCl; purchased from VWR Scientific) dissolved in sterile, injectable water to a final concentration of 0.9% NaCl by weight of water.

Step 2. An amount of pure (99.999% purity) hydrochloric acid (obtained from Aldrich Chemical Company) is added to the NaCl solution of Step 1 in order to obtain a final pH in the range of approximately 2.0 to 6.0.

Step 3. An amount of U.S.P. grade potassium chloride crystals (KCl; purchased from VWR Scientific) is dissolved in the solution of Step 2 (0.9% NaCl) such that the final concentration of potassium chloride is 0.1% by weight.

Step 4. One part by weight of pure (99.999% purity) cisplatin is added to the solution of Step 3 and is completely dissolved by agitation (1500 to 2500 rpm) for approximately 60 to 90 minutes at room temperature.

Step 5. Thirty (30) parts by weight of disodium 2,2'-dithio-bis-ethane sulfonate (as produced by Example 1) is added to the solution of Step 4. This mixture is agitated until complete dissolution and the final pH ranging between approximately pH 2.0 and pH 6.0 by adding pure (99.999% purity) hydrochloric acid (purchased from Aldrich Chemical Company).

Step 6. The solution of Step 5 is sterilized via filtration through a sterile 0.22 micron filter (obtained from VWR Scientific)

Step 7. The sterile solution of Step 6 is stored in sterile injection vials wherein each vial contains approximately 1.0 mg of cisplatin and 28.7 mg of 2,2'-dithio-bis-ethane sulfonate per ml of injection solution.

Example 8

Method #6 to Produce a Sterile Solution Containing Cisplatin and 2,2'-Dithio-bis-ethane Sulfonate This example is designed to detail another method to produce a sterile solution containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. U.S.P. grade sodium chloride (NaCl; purchased from VWR Scientific) dissolved in sterile, injectable water to a final concentration of 0.9% NaCl by weight of water. A suitable amount of pure (99.999% purity) hydrochloric acid is added to the sterile, injectable 0.9% sodium chloride solution in order to obtain a final pH in the range of approximately 2.0 to 6.0.

Step 2. Pure mannitol (99+% purity, purchased from Aldrich Chemical Company) is dissolved in the solution of Step 1 so that the concentration of mannitol is 1.0% by weight.

Step 3. One part by weight of pure, cisplatin (purchased from Aldrich Chemical Company, grade 99.999% purity) is added to the admixture of Step 2. The cisplatin is allowed to completely dissolve by agitation (1500–2500 rpm) at room temperature. This should take approximately 60 to 90 minutes at room temperature.

Step 4. Then, 30 parts by weight of disodium 2,2'-dithio-bis-ethane sulfonate (as produced in Example 1) is added to the mixture of Step 3. This mixture is agitated until complete dissolution and the final pH is adjusted to a pH ranging between approximately pH 2.0 and pH 6.0 by adding pure (99.999% purity) hydrochloric acid (purchased from Aldrich Chemical Company).

Step 5. The solution of Step 4 is sterilized via filtration through a 0.22 micron filter (obtained from VWR Scientific).

Step 6. The sterile solution of Step 5 is stored in sterile injection vials wherein each vial contains approximately 0.5 mg of cisplatin and 12.9 mg of 2,2'-dithio-bis-ethane sulfonate per ml of injection solution.

Example 9

Stability of 2,2'-Dithio-bis-ethane Sulfonate and Cisplatin Formulations

This example is designed to study the stability of 2,2'-dithio-bis-ethane sulfonate and cisplatin formulations.

1. First, 2,2'-dithio-bis-ethane sulfonate-cisplatin formulations will be prepared according to Examples 3 through 8.

2. The final pH of each formulation will be adjusted to a range of 2.0 to 6.0.

3. Each pH adjusted 2,2'-dithio-bis-ethane sulfonate—cisplatin formulation will be stored in a sealed glass vial protected from fluorescent light at room temperature (approximately 27 degrees Celsius.).

4. The stability of each pH adjusted 2,2'-dithio-bis-ethane sulfonate-cisplatin formulation will be analyzed on a weekly basis for at least 6 (six) months by nuclear magnetic resonance (NMR) analysis. The NMR spectra will be compared to a freshly prepared and pH adjusted 2,2'-dithio-bis-ethane sulfonate-cisplatin formulation. Observing one peak corresponding to the freshly prepared formulation will denote stability of the pH adjusted formulation over time, as a function of pH.

The processes for making formulations of the formula I compounds and other antineoplastic agents are similar to those described above. The synthetic process for making the formula E compounds, particularly Dimesna, are outlined in United States Provisional Patent Application Ser. No.

60/028,212, filed Oct. 1, 1996, which is incorporated herein by reference. Methods for using the Formula I compounds with Platinum complex antineoplastic agents are outlined in one or more of the copending parent applications.

It is noteworthy that, while mechanisms of action of both antineoplastic agents and the toxicity reduction features of the formula I compounds have been postulated, the disclosure of these purported mechanisms is not intended to be binding upon the inventors as indicative of the underlying reasons which explain the usefulness of the formula I compounds. As with most antineoplastic agents, where the exact mechanism(s) of action is not a certainty, the mechanism(s) of protection by which the formula I compounds reduce the toxicity of the antineoplastic agents is not as yet fully understood. However, the above disclosures concerning physiological mechanisms of action constitute the best information known at this time.

What is claimed is:

1. A pharmaceutical formulation comprising a solution or suspension of i) an effective amount of an Anthracycline or Anthracenedione antineoplastic agent; and ii) a compound of the formula:

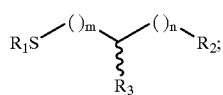
(I)

wherein:

$R_1$ is hydrogen, lower alkyl or

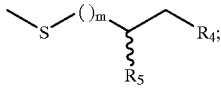

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof, and one or more pharmaceutically acceptable carriers, excipients or diluents.

2. The pharmaceutical formulation of claim 1 wherein said Anthracycline or Anthracenedione is Doxorubicin.

3. The pharmaceutical formulation of claim 1 wherein said Anthracycline or Anthracenedione is Daunorubicin.

4. The pharmaceutical formulation of claim 1 wherein said Anthracycline or Anthracenedione is Epirubicin or Mitoxantrone.

5. A method of reducing the toxicity of an Anthracycline or Anthracenedione administered to a patient as therapy for cancer, said method comprising administering to said patient an effective amount of said Anthracycline or Anthracenedione, and a toxicity reducing amount of a compound of the formula:

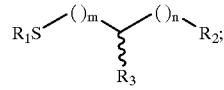
(I)

wherein:

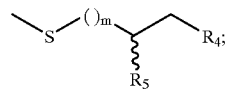

$R_1$ is hydrogen, lower alkyl or $R_2$ and $R_4$ are each individually $SO_3^-M^+$, $PO_3^{2-}M_2^{2+}$ or $PO_2S^{2-}M_2^{2+}$;

$R_3$ and $R_5$ are each individually hydrogen, hydroxy or sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof.

6. The method of claim 5 wherein said formula I compound is administered to said patient at a time from five minutes prior to sixty minutes prior to administration of the anthracenedione agent.

7. The method of claim 5 wherein said formula I compound is administered to said patient at a time from fifteen minutes prior to thirty minutes prior to administration of the anthracenedione.

8. The method of claim 5 wherein said formula I compound is administered to said patient simultaneously with the anthracenedione agent.

9. The method of claim 5 wherein said formula I compound is administered to said patient intravenously.

10. The method of claim 5 wherein said formula I compound is administered to said patient orally.

11. The method of claim 9 wherein said anthracenedione agent is administered parenterally.

12. The method of claim 10 wherein said anthracenedione agent is administered parenterally.

13. The method of claim 10 wherein said anthracenedione agent is administered orally.

14. The method of claim 5 wherein said Anthracycline or Anthracenedione is Doxorubicin.

15. The method of claim 5 wherein said Anthracycline or Anthracenedione is Daunorubicin.

16. The method of claim 5 wherein said Anthracycline or Anthracenedione is Epirubicin or Mitoxantrone.

17. A method of reducing the toxicity of an Anthracycline or Anthracenedione comprising administering to a patient in need of Anthracycline or Anthracenedione therapy an effective amount of the Anthracycline or Anthracenedione, and an effective amount of a formula I compound:

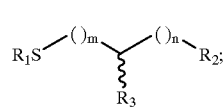
(I)

wherein:

$R_1$ is hydrogen, lower alkyl or

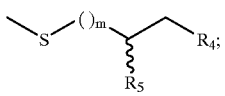

$R_2$ and $R_4$ are each individually $SO_3^-M^+$, $PO_3^{2-}M_2^{2+}$, or $^-PO_2S^{2-}M_2^{2+}$;

$R_3$ and $R_5$ are each individually hydrogen, hydroxy or sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof;

wherein the effective amount of the formula I compound is from four times by weight greater to five thousand times by weight greater than the amount of the Anthracycline or Anthracenedione administered.

18. The method of claim 17 wherein said Anthracycline or Anthracenedione is Doxorubicin.

19. The method of claim 17 wherein said Anthracycline or Anthracenedione is Daunorubicin.

20. The method of claim 17 wherein said Anthracycline or Anthracenedione is Epirubicin or Mitoxantrone.

* * * * *